(12) United States Patent
Kwon

(10) Patent No.: US 9,702,947 B2
(45) Date of Patent: Jul. 11, 2017

(54) MRI ACOUSTIC SYSTEM, ACOUSTIC OUTPUT DEVICE, AND ELECTRO-ACOUSTIC TRANSDUCER

(71) Applicant: SAMSUNG ELECTRONICS CO., LTD., Suwon-si (KR)

(72) Inventor: Oh-soo Kwon, Gunpo-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 113 days.

(21) Appl. No.: 14/459,839

(22) Filed: Aug. 14, 2014

(65) Prior Publication Data

US 2014/0354283 A1  Dec. 4, 2014

Related U.S. Application Data

(63) Continuation-in-part of application No. 13/863,637, filed on Apr. 16, 2013.

(30) Foreign Application Priority Data

Oct. 24, 2012  (KR) .................. 10-2012-0118671

(51) Int. Cl.
  *G01V 3/00*  (2006.01)
  *G01R 33/28*  (2006.01)
  *A61B 5/055*  (2006.01)
(52) U.S. Cl.
  CPC ............ *G01R 33/283* (2013.01); *A61B 5/055* (2013.01)
(58) Field of Classification Search
  CPC .................................................. G01R 33/283
  (Continued)

(56) References Cited

U.S. PATENT DOCUMENTS

| 4,689,565 A | 8/1987 | Kemner et al. |
| 5,450,499 A | 9/1995 | Morris, Sr. et al. |

(Continued)

FOREIGN PATENT DOCUMENTS

| CN | 1298487 A | 6/2001 |
| CN | 1367378 A | 9/2002 |

(Continued)

OTHER PUBLICATIONS

Communication dated Nov. 27, 2013 issued by the Korean Intellectual Property Office in counterpart Korean Patent Application No. 10-2012-0118671.

(Continued)

*Primary Examiner* — Louis Arana
(74) *Attorney, Agent, or Firm* — Sughrue Mion, PLLC

(57) ABSTRACT

Provided is magnetic resonance imaging (MRI) acoustic system that includes a magnet that is included in a bore having an image-taking space where an object is able to be accommodated and that forms a magnetic field in the image-taking space to obtain an MR image of the object, an electro-acoustic transducer that is located outside of the bore, and includes coils through which a current for generating an attraction force or a repulsion force with respect to the magnetic field generated by the magnet and a vibrating plate that vibrates in response to the an attraction force or the repulsion force, and a controller that controls the intensity of the current inputted to the electro-acoustic transducer to generate a sound by using the magnetic field that is generated by the magnet.

11 Claims, 22 Drawing Sheets

(58) Field of Classification Search
USPC .................................................. 324/318, 322
See application file for complete search history.

(56) References Cited

U.S. PATENT DOCUMENTS

| | | | |
|---|---|---|---|
| 5,481,192 | A | 1/1996 | Mehlkopf et al. |
| 6,396,268 | B1 | 5/2002 | Hinks et al. |
| 6,441,616 | B1 | 8/2002 | Mansfield |
| 8,867,756 | B2 * | 10/2014 | Zenge ............... A61B 7/04 381/67 |
| 2003/0112985 | A1 | 6/2003 | Baumgart et al. |
| 2003/0161494 | A1 | 8/2003 | Baumgart et al. |
| 2009/0208029 | A1 | 8/2009 | Porzelt et al. |
| 2010/0231483 | A1 | 9/2010 | Bazih et al. |
| 2010/0238362 | A1 | 9/2010 | Hughes et al. |
| 2015/0100310 | A1 * | 4/2015 | Cha ................... G10L 21/0208 704/228 |

FOREIGN PATENT DOCUMENTS

| | | |
|---|---|---|
| DE | 19727657 C1 | 1/1999 |
| DE | 103 43 006 A1 | 4/2005 |
| EP | 0 170 307 A1 | 2/1986 |
| JP | 6-261888 A | 9/1994 |
| JP | 2005-051284 A | 2/2005 |
| JP | 2007-307124 A | 11/2007 |
| JP | 2009-195649 A | 9/2009 |
| KR | 10-2009-0022482 A | 3/2009 |

OTHER PUBLICATIONS

Communication dated Nov. 29, 2013, issued by the European Patent Office in counterpart European Patent Application No. 13165385.9.

M. Bischoff et al; "Utilizing the ventriloquism-effect to investigate audio-visual binding"; Neuropsychologia; XP005730951; vol. 45; No. 3; Dec. 14, 2006; pp. 578-586.

Frank Baumgart et al; "Electrodynamic headphones and woofers for application in magnetic resonance imaging scanners"; Medical Physics; XP012010341; vol. 25; No. 10; Oct. 1, 1998; pp. 2068-2070.

Communication dated Apr. 29, 2016, issued by the State Intellectual Property Office of P.R. China in counterpart Chinese Application No. 201310276985.6.

CalcTool: Solenoid properties calculator, downloaded Feb. 3, 2017, from www.calctool.org/CALC/phys/electromagnetism/solenoid, 1 page.

The Second Office Action issued Dec. 15, 2016, in corresponding CN Application No. 201310276985.6, 21 pages in English and Chinese.

* cited by examiner

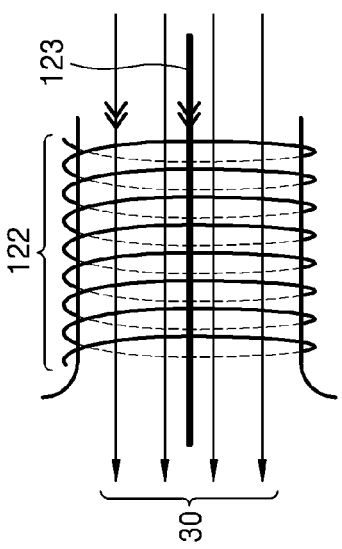
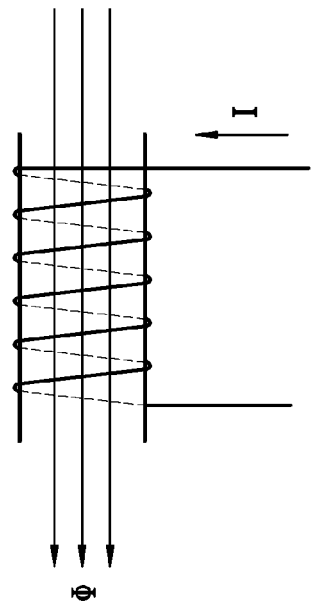
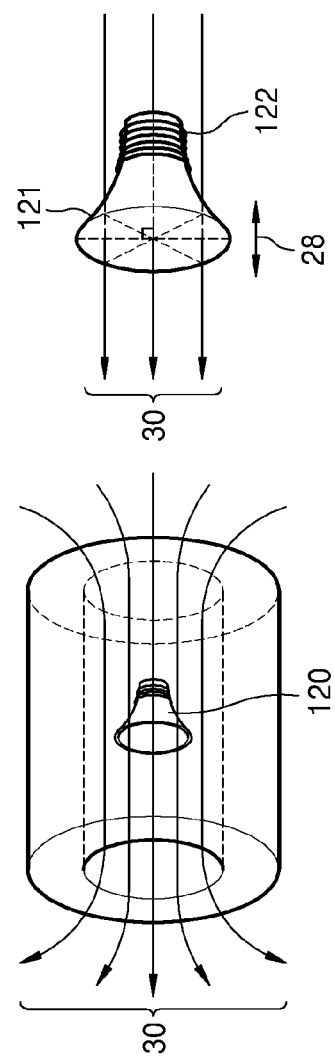
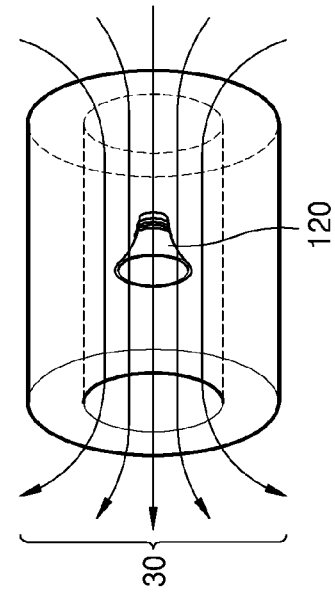

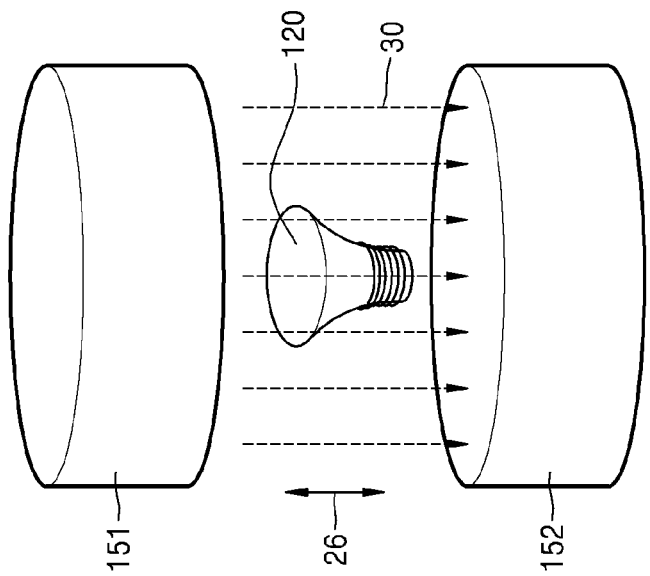
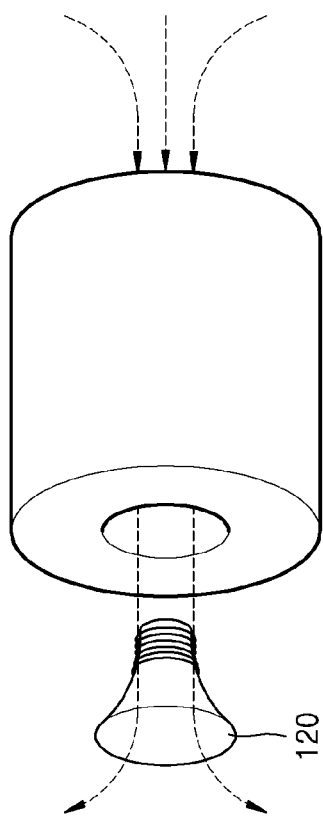

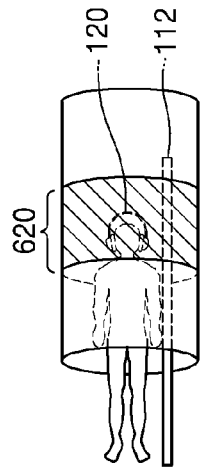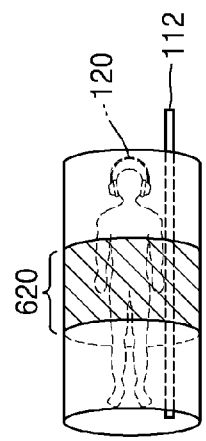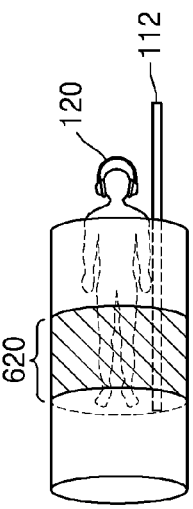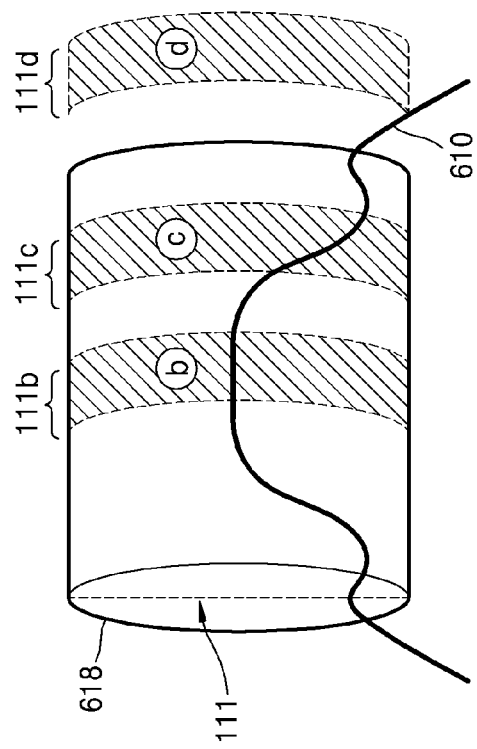

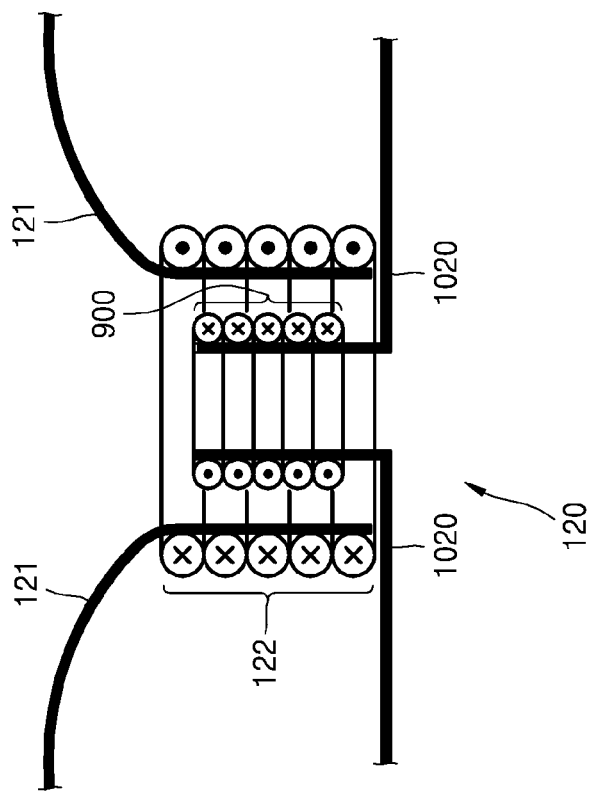
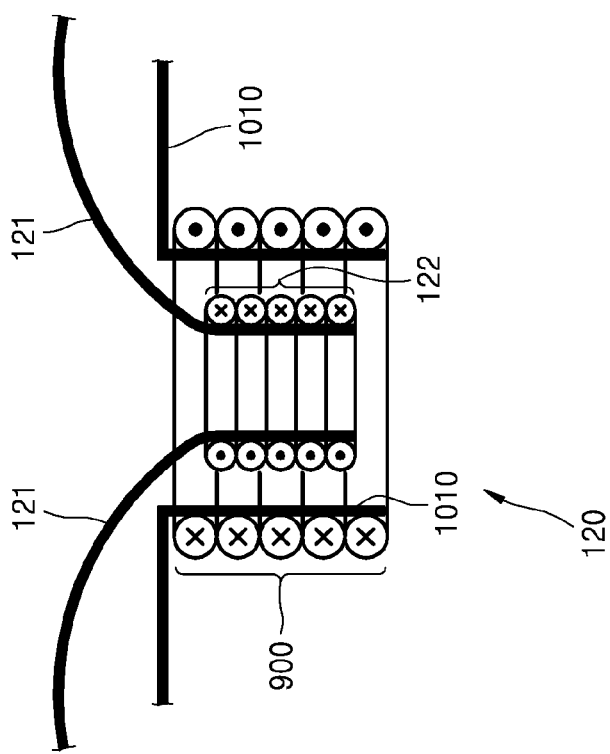

MRI ACOUSTIC SYSTEM, ACOUSTIC OUTPUT DEVICE, AND ELECTRO-ACOUSTIC TRANSDUCER

CROSS-REFERENCE TO RELATED PATENT APPLICATION

This application is a continuation-in-part application of U.S. application Ser. No. 13/863,637, which claims the priority from Korean Patent Application No. 10-2012-0118671, filed on Oct. 24, 2012, in the Korean Intellectual Property Office, the disclosure of which is incorporated herein in its entirety by reference.

BACKGROUND

1. Field

Methods and apparatuses consistent with exemplary embodiments relate to a magnetic resonance imaging (MRI) acoustic system, and more particularly, to an MRI acoustic system including an acoustic output device and an electro-acoustic transducer that operate based on a magnetic field of the MRI acoustic system.

2. Description of the Related Art

A magnetic resonance (MR) image is obtained through magnetic resonance of an atomic nucleus in a magnetic field. Resonance of an atomic nucleus is a phenomenon where the atomic nucleus in a lower energy state changes to a higher energy state by absorbing high frequency energy when specific high frequency energy is irradiated to the atomic nucleus that is in a magnetized state due to an external magnetic field. Atomic nucleuses have different resonance frequencies according to their types, and the resonance is affected by the intensity of the external magnetic field. There are a large number of atomic nucleuses in the human body, and generally, a hydrogen atomic nucleus is used for MRI.

An MRI apparatus is non-invasive, has a superior tissue contrast compared to the computed tomography (CT), and generates no artifacts due to bone structure. The MRI apparatus may take various cross-sectional images in desired directions without changing the position of a shooting object. Thus, the MRI apparatus is widely used together with other image imaging apparatuses.

A dynamic speaker, a loud speaker, or a piezo-electric speaker is used as an electro-acoustic transducer for outputting an acoustic signal to a patient undergoing medical diagnosis by using the MRI apparatus.

A loud speaker or a piezo-electric speaker is mainly used as an acoustic outputting device for an MRI apparatus. However, a magnetic material in the loud speaker may affect the magnetic field of the MRI apparatus, and the piezo-electric speaker has a limited number of frequency bands for sound output and is expensive.

There is a need to develop an electro-acoustic transducer and an acoustic output device with the decreased production cost, improved sound quality, consistent low sound generation ability, and lessened degree of effect on the quality of an MRI image.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

According to an aspect of an exemplary embodiment, there is provided an MRI acoustic system including: an MRI apparatus that includes a magnet; an electro-acoustic transducer that includes a coil through which a current flows so that an attractive force or a repulsive force is generated with respect to the magnet and a vibrating plate that is combined with the coil and vibrates in response to the attractive force or the repulsive force; and a controller that controls the intensity of a current input to the electro-acoustic transducer according to a horizontal position of the electro-acoustic transducer in a magnetic field generated by the magnet.

The MRI acoustic system may further include a storage that stores in advance an intensity of the current according to the horizontal position of the electro-acoustic transducer, the controller controlling the intensity of the current so that the vibrating plate vibrates regardless of an intensity of the magnetic field according to a change of the horizontal position of the electro-acoustic transducer.

The MRI acoustic system may further include a detector that detects an intensity of the magnetic field, the controller blocking the current input to the electro-acoustic transducer when the intensity of the magnetic field is detected to be below a critical value.

The controller may block the current input to the electro-acoustic transducer when the horizontal position of the electro-acoustic transducer is outside of a predetermined range.

The MRI acoustic system may further include a filter that prevents interference between radio-frequency (RF) signals generated from the MRI apparatus and the electro-acoustic transducer.

The electro-acoustic transducer may be disposed so that a vibrating direction of the vibrating plate and a direction of a magnetic flux focused by the magnet are not perpendicular to each other.

The electro-acoustic transducer may be positioned in the magnetic field formed by the magnet so that a central axis of the coil and a direction of a magnetic flux focused by the magnet are not perpendicular to each other.

The electro-acoustic transducer may be positioned on a head portion of a cradle where the patient is located to move in the magnetic field.

The controller may control an intensity of the current according to a moving distance of the cradle into the magnetic field of the MRI apparatus, the electro-acoustic transducer is being positioned on the cradle.

The electro-acoustic transducer may be mounted on a head RF coil of the MRI apparatus.

The electro-acoustic transducer may be mounted on a headset or an earphone of the MRI apparatus.

The MRI acoustic system may further include a detector that detects the intensity of the magnetic field, the controller controlling the intensity of the current according to the intensity of the detected magnetic field.

According to an aspect of an exemplary embodiment, there is provided an acoustic output device that uses a magnetic field of the MRI apparatus, including: a coil through which a current for generating an attractive force or a repulsive force with respect to a magnet of the MRI apparatus flows; a vibrating plate that is combined with the coil and vibrates according to the attractive force or the repulsive force; and a controller that controls an intensity of an input current that flows through the coil in the magnetic field according to a horizontal position of the electro-acoustic transducer.

The acoustic output device may further include a storage that stores in advance an intensity of the input current according to the horizontal position of the electro-acoustic transducer, the controller controlling the intensity of the input current so that the vibrating plate vibrates regardless of the intensity of the magnetic field according to the horizontal position of the electro-acoustic transducer.

The acoustic output device may further include a detector that detects the intensity of the magnetic field, the controller blocking the current input to the electro-acoustic transducer when the intensity of the magnetic field is detected to be below a critical value.

The controller may block the current input to the electro-acoustic transducer when the horizontal position of the electro-acoustic transducer is outside of a predetermined range.

The acoustic output device may further include a headset or an earphone.

According to an aspect of an exemplary embodiment, there is provided an electro-acoustic transducer that uses a magnetic field of an MRI apparatus, including: a first coil through which a current for generating an attractive force or a repulsive force with respect to the MRI apparatus flows; a second coil for reducing a magnetic field generated by the current that flows in the first coil; and a vibrating plate that is combined with the first coil and vibrates according to the attractive force or the repulsive force.

A current having a predetermined intensity may flow through the second coil to reduce the magnetic field generated by the first coil.

The second coil may be wound by a predetermined number of turns for reducing the magnetic field generated by the first coil.

The electro-acoustic transducer may further include a fixing unit that fixes the second coil, wherein the second coil has a concentric axis with the first coil and is combined with the fixing unit on an inner side or outer side of the first coil.

The direction of a current that flows through the second coil may be opposite to the direction of a current that flows through the first coil.

The electro-acoustic transducer may be positioned on a head portion of a cradle where the patient is located in the MRI apparatus.

The electro-acoustic transducer may be mounted on a head RF coil of the MRI apparatus.

The electro-acoustic transducer may be mounted on a headset or an earphone of the MRI apparatus.

According to an aspect of an exemplary embodiment, there is provided an acoustic system that includes the electro-acoustic transducer described above.

According to an aspect of an exemplary embodiment, there is provided an electro-acoustic transducer that uses a magnetic field of an MRI apparatus, including: a vibrating unit that vibrates according to a Lorentz force generated by the magnetic field; a supporting unit that fixes both edges of the vibrating unit; and a first coil that is disposed on the vibrating unit and vibrates together with the vibrating unit.

The electro-acoustic transducer may further include a second coil that is fixed on the supporting unit and is combined with the first coil.

The electro-acoustic transducer may include at least one first coil and at least one second coil, wherein the at least one first coil and the at least one second coil are combined with each other and are disposed along at least one surface of the supporting unit and the vibrating unit.

The first coil and the second coil may be parallel to each other, and currents respectively flow therethrough in opposite directions.

The first coil may include a thin film coil formed on the vibrating unit.

The vibrating unit may include a first vibrating unit and a second vibrating unit disposed in parallel to the first vibrating unit, both edges of the first vibrating unit and both edges of the second vibrating unit being respectively combined with the supporting unit, and the first coil being disposed on the first and second vibrating units.

The first coil may be disposed on the vibrating unit in at least one repeating pattern.

The first coils may be disposed so that a location of the center of the repeating pattern is biased on a side of the first coils.

The vibrating unit may include a vibrating plate that vibrates due to the Lorentz force and is separated from the supporting unit, and a connection unit that connects the vibrating plate to the supporting unit, wherein the first coil is disposed on the vibrating plate.

The vibrating unit may include a vibrating film that vibrates due to the Lorentz force.

The vibrating unit may include a vibrating plate that vibrates due to the Lorentz force and is formed of an elastic member.

The electro-acoustic transducer may be positioned on a head portion of a cradle where the patient is positioned in the MRI apparatus.

The electro-acoustic transducer may be mounted on a head RF coil of the MRI apparatus.

The electro-acoustic transducer may be mounted on a headset or an earphone of the MRI apparatus.

According to an aspect of an exemplary embodiment, there is provided an electro-acoustic transducer that uses a magnetic field of an MRI apparatus, including: a vibrating unit that vibrates according to an attractive force or a repulsive force with respect to a magnet of the MRI apparatus; a first coil that is disposed on the vibrating unit in at least one repeating pattern and through which a current for generating the attractive force or the repulsive force flows; and a second coil that is combined with the first coil, and through which a current input to the first coil and a current output from the first coil flows.

The pattern may include a screw shape pattern.

The pattern may include a rectangular shape pattern.

The patterns may be formed by consecutively disposing the first coils along a predetermined direction on the vibrating unit.

The second coil may be disposed on a lower surface of the vibrating unit.

According to an aspect of an exemplary embodiment, there is provided an MRI acoustic system including: a magnet that is included in a bore having an image-taking space where an object is able to be accommodated and that forms a magnetic field in the image-taking space to obtain an MR image of the object; an electro-acoustic transducer that is located outside of the bore, and comprises coils through which a current for generating an attraction force or a repulsion force with respect to the magnetic field generated by the magnet and a vibrating plate that vibrates in response to the attraction force or the repulsion force; and a controller that controls the intensity of the current inputted to the electro-acoustic transducer to generate a sound by using the magnetic field that is generated by the magnet.

The electro-acoustic transducer may be located outside of the bore so that the direction of a current that flows through the coils is not parallel to the magnetic field generated by the magnet.

The bore may have a column shape, the image-taking space in the bore may be configured to accommodate the object through an opening in at least one of a top surface and a bottom surface of the bore, the electro-acoustic transducer may be located on at least one of the top surface and the bottom surface of the bore.

The electro-acoustic transducer may be located on at least one of the top surface and the bottom surface of the bore so that the direction of a current that flows through the coils is perpendicular to the magnetic field generated by the magnet.

The electro-acoustic transducer may be configured so that the vibrating plate vibrates in a direction parallel to the direction of moving a cradle for accommodating the object in the image-taking space.

According to an aspect of an exemplary embodiment, there is provided an electro-acoustic transducer that uses a magnetic field of an MRI apparatus, the electro-acoustic transducer including: a plurality of first coils through which a current for generating an attraction force or a repulsion force with respect to the magnetic field of the MRI apparatus; a vibrating plate on which at least a portion of each of the first coils is located and that vibrates in response to the attraction force or the repulsion force generated by the first coils; a supporting unit that fixes the vibrating plate; a connection unit that connects the vibrating plate and the supporting unit; and a second coil that is combined with the first coils, and through which a current outputted from at least one of the first coils and a current inputted to one of the remaining first coils flow.

At least a portion of each of the first coils may be located on the upper surface of the vibrating plate, the remaining portion of each of the first coils may be located on upper surfaces of the supporting unit and the connection unit, at least a portion of the second coil may be located on a lower surface of the vibrating plate; and the remaining portion of the second coil may be located on lower surfaces of the supporting unit and the connection unit.

Each of the first coils may be disposed in repeated patterns.

According to an aspect of an exemplary embodiment, there is provided an MRI acoustic system that comprises an electro-acoustic transducer described in above.

BRIEF DESCRIPTION OF THE DRAWINGS

The above and/or other aspects will become more apparent by describing certain exemplary embodiments with reference to the accompanying drawings, in which:

FIGS. 4A, 4B, 4C, and 4D show positioning of an electro-acoustic transducer according to an exemplary embodiment;

FIGS. 5A and 5B are perspective views of an electro-acoustic transducer and an MRI apparatus according to an exemplary embodiment;

FIGS. 6A, 6B, 6C, and 6D show control of intensity of an input current according to horizontal positions of a cradle;

FIGS. 10A and 10B show a structure of an electro-acoustic transducer according to an exemplary embodiment;

DETAILED DESCRIPTION

Figure 1B:
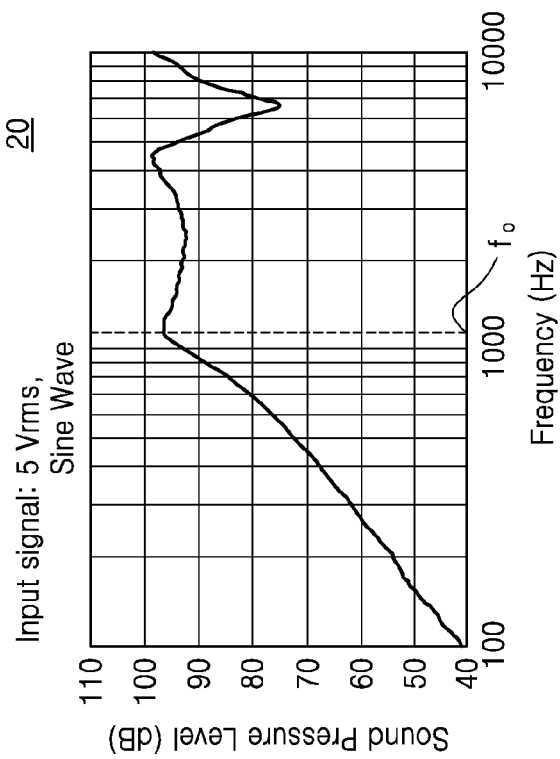
FIGS. 1A and 1B are drawings to illustrate and explain operation of a related art electro-acoustic transducers of an MRI system.

Below, certain exemplary embodiments are described in greater detail with reference to the accompanying drawings.

In the following description, like reference numerals are used for the like elements, even in different drawings. The matters defined in the description, such as detailed construction and elements, are provided to assist in a comprehensive understanding of exemplary embodiments. However, exemplary embodiments can be carried out without those specifically defined matters. Also, well-known functions or constructions are not described in detail since that would obscure the description with unnecessary detail.

The terms used herein may vary according to the intention of one of ordinary skill in the art, the precedent, or the emergence of new technologies. It should be understood that "comprises," "comprising," "includes," and/or "including" means an inclusion of other additional elements.

An "object" may include a person or a thing to be inspected, or may include portions of a person or a thing to be inspected. For example, the object may be a part of a human body of a person to be inspected, and may include an organ, such as liver, heart, womb, breast, or abdomen.

FIG. 1 is a drawing illustrating a related art electro-acoustic transducer of an MRI system.

Figure 1A:
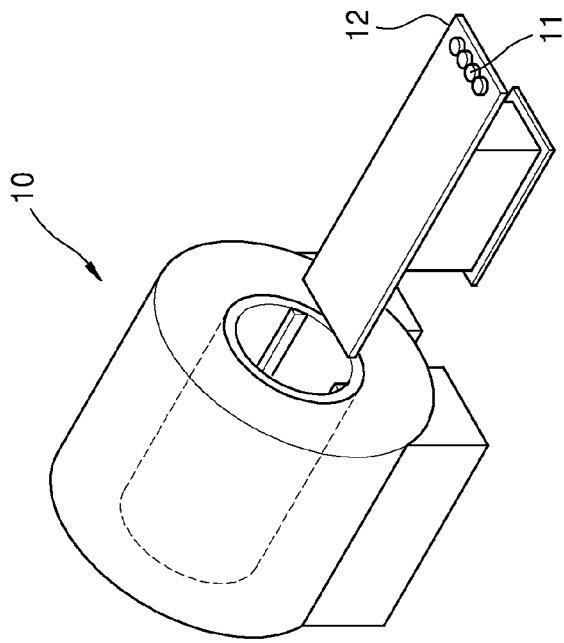

FIG. 1A is a perspective view showing an MRI apparatus 10 having a dynamic speaker 11. The dynamic speaker 11 is an acoustic output device of the MRI system. The dynamic speaker 11 has a high acoustic performance, but includes a magnetic body such as an iron or a permanent magnet.

Accordingly, the dynamic speaker 11 is positioned at a location far from a bore of the MRI apparatus in order to minimize its effect on a magnetic field of the MRI system. For example, the dynamic speaker 11 is positioned at the outside or an edge portion 12 of a cradle where an object to be diagnosed is located, and a sound output from the dynamic speaker 11 is transmitted to an object through an acoustic path provided in the cradle. Accordingly, the sound of the dynamic speaker 11 may be distorted due to the long transmission path and includes noise.

FIG. 1B shows a graph 20 of an acoustic characteristic of a piezo-electric speaker of the MRI system. The piezo-electric speaker is formed of a piezo-electric ceramic, which is a non-magnetic material that contracts/expands in response to an input electric signal, and thus, is installed inside a bore since it does not nearly affect a magnetic field of the MRI apparatus.

However, as depicted in graph 20, generally, a resonance frequency f0 of the piezo-electric speaker is greater than 1 kHz, which is greater than that of the dynamic speaker 11. Accordingly, due to the difficulties to generate a low sound and the difficulties to make a wide-width electrode of the piezo-electric speaker, it is difficult to transmit an RF signal of the MRI apparatus to a speaker, and thus, a distortion of an MRI image may occur. Also, the piezo-electric speaker that includes a piezo-electric ceramic, which is a non-magnetic material, has a production cost higher than that of the dynamic speaker 11.

Figure 2:
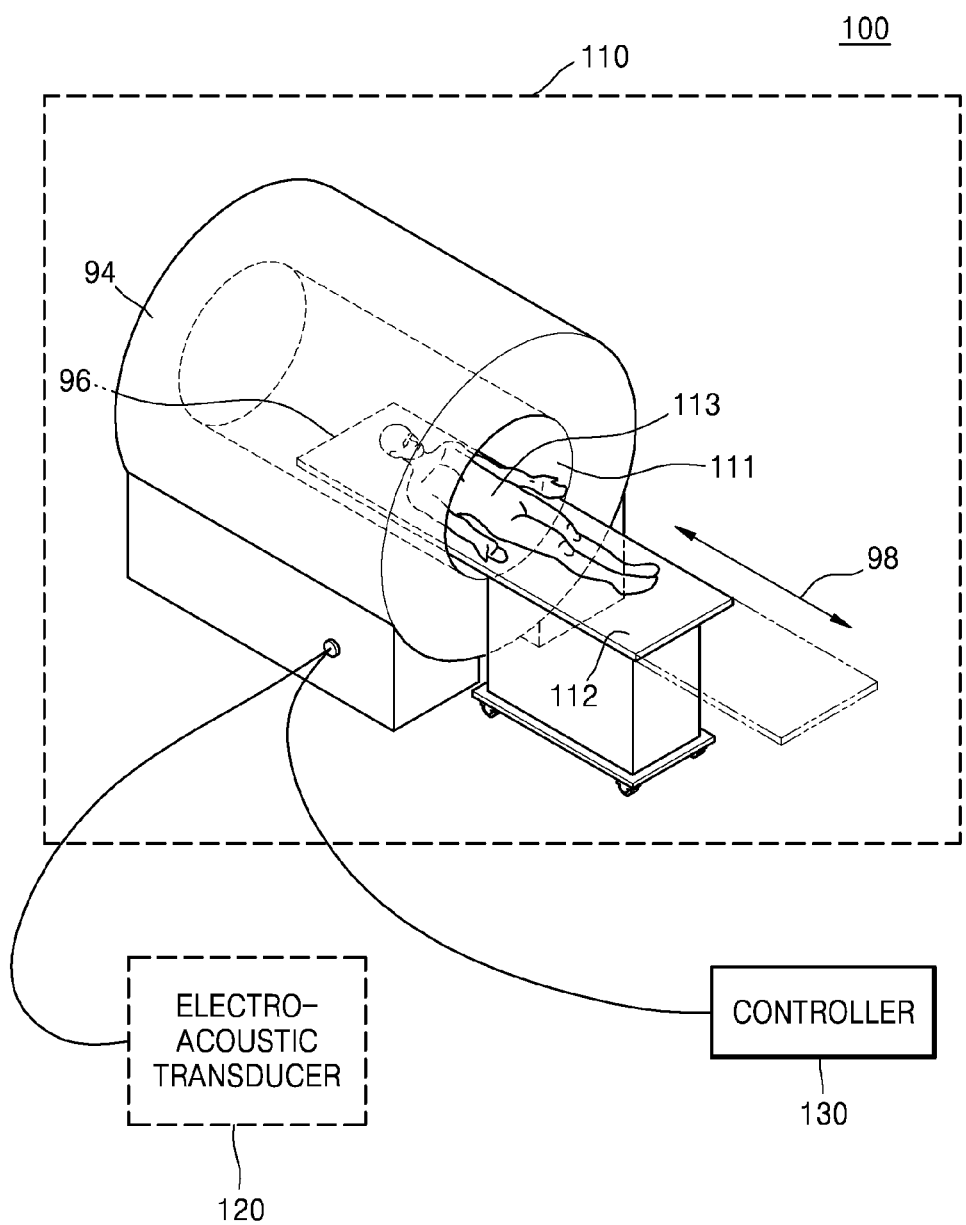
FIG. 2 illustrates an MRI acoustic system according to an exemplary embodiment.

FIG. 2 illustrates an MRI acoustic system 100 according to an exemplary embodiment. The MRI acoustic system 100 may include an MRI apparatus 110, an electro-acoustic transducer 120, and a controller 130. The MRI acoustic system 100 may further include other elements besides the elements depicted in FIG. 2.

The MRI apparatus 110 is used to diagnose a patient 113 positioned on a cradle 112 by using a magnetic field generated from a magnet. The MRI apparatus 110 generates an MRI image of the patient 113 by processing a magnetic resonance signal received from the patient 113 placed in the magnetic field, and may display an MRI image on a screen. The MRI apparatus 110 may include a bore 111 that includes an image-taking space that may accommodate an object. The object denotes at least a part of the patient 113 that is positioned on a cradle 112. The bore 111 of the MRI apparatus 110 may include may include a magnet that forms a magnetic field in the image-taking space for obtaining MR image.

The bore 111 according to the exemplary embodiment may have a column shape. For example, as depicted in FIG. 2, the bore 111 may have a cylinder shape. An image-taking space in the bore 111 may be configured to accommodate an object through an opening that is included in at least one of a top surface and a bottom surface of the bore 111 having a column shape. For example, as depicted in FIG. 2, the MRI apparatus 110 may have a column shape that includes two donut shape bottoms. The bore 111 may allow moving the patient 113 that is positioned on the cradle 112 through the image-taking space that penetrate through the bore 111 and may obtain an MR image of the patient 113.

The MRI apparatus 110 includes a superconducting magnet or a permanent magnet as an element for generating a magnetic field. In the case of the superconducting magnet, liquid helium may be used as refrigerant. Also, with respect to the superconducting magnet, liquid nitrogen or a conduction cooling method may be used besides the liquid helium. The MRI apparatus 110 may be located in a room shielded from external RF signals by being separated from an operating room where a radiologist controls the operation of the MRI apparatus 110.

The electro-acoustic transducer 120 generates an acoustic signal via the magnetic field of the MRI apparatus 110. The acoustic signal generated from the electro-acoustic transducer 120 is transmitted to a user, and the electro-acoustic transducer 120 may transmit a signal from the user of the MRI apparatus 110 to the patient 113. Hereinafter, the "acoustic signal" denotes a sound wave generated by vibration of a vibrating plate of the electro-acoustic transducer 120. However, the "acoustic signal" is not limited thereto, and may denote any predetermined signal electrically generated.

The electro-acoustic transducer 120 may include a coil through which a current flows for generating an attractive force or a repulsive force with respect to a magnet of the MRI apparatus 110, and a vibrating plate that is combined to the coil to vibrate according to the attractive force or repulsive force. A configuration of the electro-acoustic transducer 120 and an operation of generating an acoustic signal by vibrating are described with reference to FIG. 4.

Furthermore, according to an exemplary embodiment, the electro-acoustic transducer 120 may include a non-magnetic vibration film instead of the vibrating plate, which vibrates according to a force that interacts with the magnetic field of the MRI apparatus 110. This embodiment will be described with reference to FIGS. 11 through 13.

The electro-acoustic transducer 120 according to an exemplary embodiment may be located at least one of outsides of a bore 111 and inside the bore 111. The electro-acoustic transducer 120 according to an exemplary embodiment generates an acoustic signal via the magnetic field of the magnet of the MRI apparatus 110 instead of a magnetic material of a dynamic speaker. Accordingly, since the electro-acoustic transducer 120 does not affect the magnetic field of the MRI apparatus 110, the electro-acoustic transducer 120 may be located in the bore 111.

The controller 130 may control the intensity of a current that is inputted to the electro-acoustic transducer 120 so that an acoustic signal is generated by using a magnetic field generated by a magnet of the MRI apparatus 110. The controller 130 may control an intensity of a current input to the electro-acoustic transducer 120 according to a horizontal position of the electro-acoustic transducer 120. That is, the controller 130 may control the intensity of the current input to the electro-acoustic transducer 120 to generate an acoustic signal according to the horizontal position of the electro-acoustic transducer 120 on the MRI apparatus 110. The "horizontal position" may denote a position in a horizontal direction of the electro-acoustic transducer 120, i.e., a direction substantially parallel to a movement of the cradle 112 in the bore 111 of the MRI apparatus 110. Accordingly, the horizontal position may be changed according to the movement of the cradle 112 in the bore 111 or according to the position change of the patient 113 on the cradle 112.

More specifically, the patient 113 is positioned on the cradle 112, and the cradle 112 moves into the bore 111 of the MRI apparatus 110 to control a position of the patient 113. That is, as depicted in FIG. 2, the cradle 112 may move in the magnetic field to image an region of interest (ROI), for example, knee, neck, waist, etc., of the patient 113, in a horizontal direction 98, toward the end portion 94 of the bore 111 or away from the end portion 94 of the bore 111.

As described above, the electro-acoustic transducer 120 is driven by an attractive force or a repulsive force between the magnetic field generated by an input current and the magnet of the MRI apparatus 110. That is, when an intensity of the current input to the electro-acoustic transducer 120 increases, the intensity of the magnetic field generated by the electro-acoustic transducer 120 is increased, and thus, the intensity of a force interacting with the magnet of the MRI apparatus 110 is changed. Accordingly, the intensity of the input current is related to the intensity of an acoustic signal generated by the electro-acoustic transducer 120. As the intensity of input current increases, the intensity of an acoustic signal also increases.

The controller 130 controls the intensity of a current input (hereinafter, input current) to the electro-acoustic transducer 120 according to the horizontal position of the electro-acoustic transducer 120 in the magnetic field, and thus, the intensity of the acoustic signal generated by the electro-acoustic transducer 120 may be controlled. The current exemplary embodiment is described below in detail with reference to FIG. 6.

As described with reference to FIG. 1, the dynamic speaker of a related art MRI acoustic system 100 is located away from the bore since the dynamic speaker may affect the magnetic field of the MRI apparatus. Accordingly, if the patient is positioned away from the dynamic speaker, the length of a transmission path of the acoustic signal is increased, and thus, the degree of distortion of the acoustic signal is increased.

However, according to the MRI acoustic system 100 depicted in FIG. 2, the electro-acoustic transducer 120 does not affect the magnetic field of the MRI apparatus 110, and in the MRI apparatus 110, the intensity of the acoustic signal generated by the electro-acoustic transducer 120 may be controlled according to the horizontal position of the cradle 112. Accordingly, regardless of the position of the patient within the bore 111, an acoustic signal with constant intensity may be transmitted to the patient 113.

The electro-acoustic transducer 120 depicted in FIG. 2 may be mounted on an acoustic output device 126. For example, the electro-acoustic transducer 120 may be provided on various acoustic output devices 126 such as a headset or an earphone. According to an exemplary embodiment, the electro-acoustic transducer 120 may also be provided on a head RF coil of the MRI apparatus 110 or on a head portion 96 of the cradle 112 where the patient 113 is positioned.

Figure 3:
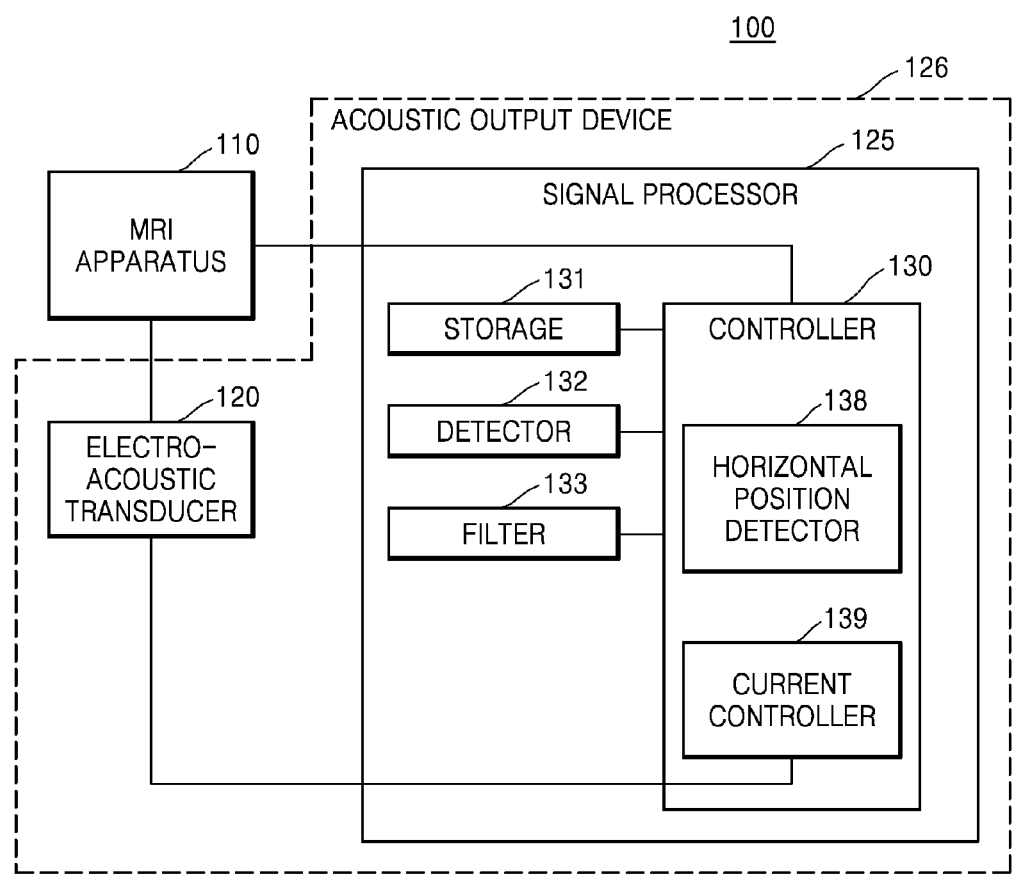
FIG. 3 is a block diagram showing a configuration of an MRI acoustic system according to an exemplary embodiment.

FIG. 3 is a block diagram showing a configuration of the MRI acoustic system 100 according to an exemplary embodiment. The MRI acoustic system 100 of FIG. 3 includes a signal processor 125 that includes a storage 131, a detector 132, and a filter 133 in addition to the MRI apparatus 110, the electro-acoustic transducer 120, and the controller 130 described with reference to FIG. 2. Descriptions of the MRI apparatus 110, the electro-acoustic transducer 120, and the controller 130 made with reference to FIG. 2 will not be repeated.

As depicted in FIG. 3, the controller 130 may include a horizontal position detector 138 and a current controller 139. Hereinafter, in addition to the description about the controller 130 of FIG. 2, the horizontal position detector 138 and the current controller 139 depicted in FIG. 3 will be described.

The horizontal position detector 138 detects a horizontal position of the electro-acoustic transducer 120, that is, detects how far the electro-acoustic transducer 120 is moved into the bore 111 of the MRI apparatus 110. That is, the horizontal position detector 138 may detect a horizontal position of the electro-acoustic transducer 120 that is moved in response to an electrical signal (when a radiologist controls the MRI apparatus 110 in an operating room) or by a physical method (when the radiologist directly moves the cradle 112 before imaging starts). The horizontal position detector 138 may transmit information regarding the horizontal position of the electro-acoustic transducer 120 to the current controller 139.

Meanwhile, the horizontal position of the electro-acoustic transducer 120 may be changed according to the movement of the cradle 112 into the MRI apparatus 110. That is, according to the movement of the cradle 112 on which the patient 113 is positioned, the horizontal position in the magnetic field of the electro-acoustic transducer 120 worn by the patient 113 or provided in the cradle 112 may be changed.

For example, when the cradle 112 is moved into the bore 111 by an external electrical signal, the horizontal position detector 138 may electrically detect information regarding the horizontal position of the electro-acoustic transducer 120 by fetching the external signal that moves the cradle 112. That is, the horizontal position detector 138 may detect a horizontal position of the electro-acoustic transducer 120 that varies according to the movement of the cradle 112 into the magnetic field.

The horizontal position detector 138 may detect the position of the cradle 112 by using at least one sensor provided on a table that supports and moves the cradle 112. For example, the horizontal position detector 138 may detect a horizontal position of the electro-acoustic transducer 120 according to the movement of the cradle 112 through the sensors disposed with predetermined gaps.

Furthermore, the horizontal position detector 138 may detect a horizontal position of the electro-acoustic transducer 120 by an external input signal. That is, when a user of the MRI apparatus 110 controls a horizontal position of the electro-acoustic transducer 120 before moving the patient 113 into the bore 111, the user may manually input a horizontal position. Afterwards, the horizontal position detector 138 may detect a horizontal position of the electro-acoustic transducer 120 by obtaining information of position that is directly input by the user.

According to an embodiment of the current invention, the horizontal position detector 138 may detect a horizontal position of the electro-acoustic transducer 120 according to an intensity of a magnetic field that is detected by a detector 132 at a predetermined location.

The current controller 139 controls an intensity of a current input to the electro-acoustic transducer 120. That is, a current flows through a coil of the electro-acoustic transducer 120 so that an attractive force or a repulsive force, which is a force interacting with a magnet of the MRI apparatus 110, is generated, and thus, the current controller 139 may control the intensity of the current that is input to the coil. A force that vibrates the electro-acoustic transducer 120 increases proportional to the intensity of the input current. Therefore, the current controller 139 may control the intensity of an acoustic signal that is generated by the electro-acoustic transducer 120 by controlling the intensity of the input current.

The current controller 139 may block the input current. That is, if a current flows through the coil when the electro-acoustic transducer 120 does not need to generate an acoustic signal, an unnecessary burden may occur on the electro-acoustic transducer 120, and thus, the lifetime of the electro-acoustic transducer 120 may be reduced. According to an exemplary embodiment, the current controller 139 may block an input current being input to the electro-acoustic transducer 120 when the intensity of the magnetic field is detected to be below a critical value or when the cradle 112 is positioned outside of the predetermined horizontal position (that is, when there is no need to transmit a sound to the patient 113). The exemplary embodiment is described below in detail with reference to FIG. 6.

Hereinafter, various elements connected to the controller 130 for controlling a current input to the electro-acoustic transducer 120 will be described.

The signal processor 125 is connected to the MRI apparatus 110 and the electro-acoustic transducer 120 and generates a control signal for controlling at least one of the MRI apparatus 110 and the electro-acoustic transducer 120, and controls an operation of at least one of the MRI apparatus 110 and the electro-acoustic transducer 120 by transmitting the generated control signal.

The signal processor 125, as described with reference to FIGS. 2 and 3, may include the controller 130 that controls a current input to the electro-acoustic transducer 120 according to the horizontal position of the cradle 112 of the MRI apparatus 110. The signal processor 125 may include the storage 131, the detector 132, and the filter 133 in addition to the controller 130, and may further include other elements besides the elements depicted in FIG. 3.

The storage 131 stores various kinds of information for controlling the electro-acoustic transducer 120 or the MRI apparatus 110. For example, the storage 131 may store information regarding the intensity of magnetic field of the MRI apparatus 110, information with regard to a direction of a magnetic flux, and information regarding physical characteristics of the coil and the vibrating plate of the electro-acoustic transducer 120.

According to an exemplary embodiment, the storage 131 may store information with regard to the intensity of input current according to a horizontal position of the electro-acoustic transducer 120. That is, in an exemplary embodiment, the controller 130 may use information stored in the storage 131 to control the intensity of the input current.

More specifically, the intensity of the magnetic field of the MRI apparatus 110 varies according to the position where the magnetic field is measured in and out of the bore 111 (this will be more specifically described with reference to FIG. 6). Accordingly, the intensity of the magnetic field that affects the electro-acoustic transducer 120 varies according to a position where the electro-acoustic transducer 120 is positioned in the bore 111. As a result, the intensity of an acoustic signal generated by the electro-acoustic transducer 120 is changed. The change of the intensity may lead to a problem in that a constant intensity acoustic signal may be difficult to transmit to the user.

Accordingly, the storage 131 may store information regarding the intensity of the magnetic field that varies at an arbitrary position in the magnetic field, and may store in advance information regarding the intensity of an input current that is required for the electro-acoustic transducer 120 to generate a constant intensity acoustic signal regardless of the intensity variation (that is, the variation of the horizontal position) of the magnetic field When information that the electro-acoustic transducer 120 has moved to a predetermined position in the bore 111 is obtained by the horizontal position detector 138, the controller 130 may control the current controller 139 by using the information of the horizontal position and the intensity of an input current, which are stored in the storage 131 in advance. That is, the storage 131 may store in advance information for providing a constant acoustic signal to the user although the intensity of the magnetic field varies according to the position change of the electro-acoustic transducer 120.

The storage 131 may store information about the intensity of the input current according to the horizontal position in a table or a list. For example, after dividing the horizontal position where the electro-acoustic transducer 120 may be able to move into a plurality of sections, the storage 131 may store the intensity of the input current by matching the intensity with each of the sections. Also, after storing a relational expression between the horizontal position of the electro-acoustic transducer 120 and the intensity of the current, when the horizontal position of the electro-acoustic transducer 120 is input from the horizontal position detector 138, the storage 131 may transmit the intensity of the input current to the current controller 139 by using the stored relational expression.

The detector 132 detects the intensity the magnetic field of the MRI apparatus 110. The detector 132 may detect the intensity of the magnetic field at predetermined positions inside or outside of the bore 111. In other words, the detector 132 may detect the intensity of the magnetic field at a predetermined position inside the magnetic field according to the movement of the horizontal position of the electro-acoustic transducer 120. For example, as depicted in FIGS. 8B and 8C, when the electro-acoustic transducer 120 is positioned on a head portion of the cradle 112, the detector 132 may detect the intensity of the magnetic field at a head portion 96 of the cradle 112 (that is, at a predetermined position where the head of the patient 113 is positioned) on which the patient 113 is positioned.

The detector 132 may transmit information regarding the intensity of the detected magnetic field to the current controller 139, and as described above, the current controller 139 may block the current input to the electro-acoustic transducer 120 when the intensity of the magnetic field is detected to be below a critical value.

The detector 132 may detect the intensity of the magnetic field in various ways. For example, when the storage 131 stores in advance information regarding the intensity of the magnetic field according to the horizontal position of the electro-acoustic transducer 120, the detector 132 may obtain the intensity regarding the magnetic field from the storage 131. The detector 132 may detect a magnetic resonance phenomenon by an electromagnetic induction method or a magnetic resonance phenomenon may be measured via an intensity of light by optically pumping a low pressure steam of an alkali metal.

The detector 132 may obtain the intensity regarding the magnetic field by using data stored in advance in the storage 131, besides directly measuring the intensity of the magnetic field. That is, when the storage 131 stores a value of the intensity of the magnetic field in advance according to the horizontal position of the electro-acoustic transducer 120, the detector 132 may obtain information about the intensity of the magnetic field according to the moving distance of the electro-acoustic transducer 120 in the horizontal direction from the stored data.

The filter 133 prevents interference between an RF signal of the MRI apparatus 110 and the electro-acoustic transducer 120. That is, the filter 133 prevents occurrence of an interference phenomenon between a resonance frequency of the electro-acoustic transducer 120 and the frequency of the RF signal of the MRI apparatus 110. The filter 133 may be electrically connected to the coil of the electro-acoustic transducer 120, and may include an RLC circuit or an RC circuit. The filter 133 may protect the electro-acoustic transducer 120 and the signal processor 125 from an effect due to variation of a magnetic field that is generated in a gradient coil and an RF signal generated in an RF coil.

The signal processor 125 may control various processes for outputting a sound to the patient 113 by being connected via a wire or in a wireless manner to the electro-acoustic transducer 120.

As shown in FIG. 3, the acoustic output device 126 includes the electro-acoustic transducer 120 and the signal processor 125. That is, the acoustic output device 126 according to an exemplary embodiment includes the electro-acoustic transducer 120 that generates an acoustic signal and the signal processor 125 that controls the current input to the electro-acoustic transducer 120.

The acoustic output device 126 may be configured in various ways to generate an acoustic signal and transmit the same to the patient 113. According to an exemplary embodiment, the acoustic output device 126 may include a headset or an earphone.

The signal processor 125 may be a separate element placed outside of the acoustic output device 126. According to an exemplary embodiment, the signal processor 125 may be an external mounting device placed at a predetermined distance from the acoustic output device 126, and may be connected to the acoustic output device 126 via a wire or in a wireless manner.

FIGS. 4A, 4B, 4C, and 4D show positioning of an electro-acoustic transducer according to an exemplary embodiment.

FIG. 4A is a drawing for explaining a solenoid coil and the Ampere's Rule. As depicted in FIG. 4A, when a current flows through the solenoid coil, a magnetic field is formed around the solenoid coil, and a direction of a magnet flux is in a direction of the central axis of the solenoid coil (in a direction according to the Ampere's Rule (the right-hand screw rule)). The solenoid coil may be regarded as a magnet that generates the magnetic field by a current that flows therethrough.

FIG. 4B shows the electro-acoustic transducer 120 that uses a magnetic field of the magnet of the MRI apparatus 110 by being located in the bore 111. In FIG. 4B, the magnetic field generated by the magnet of the MRI apparatus 110 is shown by arrows 30. FIG. 4B shows an ideal magnet having a sufficient length. Accordingly, in FIG. 4B, the magnetic field in the bore 111 is uniform. However, actually, the magnetic field may not be completely uniform at each position in the bore 111.

In FIG. 4B, if the coil of the electro-acoustic transducer 120 is a solenoid coil, a magnetic field is generated in a central axis direction of the electro-acoustic transducer 120 when a current flows through the coil. The direction of the magnetic field generated by the coil of the electro-acoustic transducer 120 varies according to the direction of the current that flows through the coil. The electro-acoustic transducer 120 may be regarded as a magnet that generates a magnetic field according to a current that flows through a coil within a region where the magnetic field is distributed. Thus, as long as a magnetic field generated by the magnet of the MRI apparatus 110 reaches the electro-acoustic transducer 120, the electro-acoustic transducer 120 may operate by being positioned in the vicinity of the magnet.

Accordingly, an attractive force or a repulsive force is generated between the electro-acoustic transducer 120 and the magnet according to the direction of a current that flows through the coil. That is, when a alternating current flows through the coil, the electro-acoustic transducer 120 generates a force that is interacting with the magnet of the bore 111 according to the direction of a current that flows through the coil and the electro-acoustic transducer 120 vibrates.

FIGS. 4C and 4D are drawings showing the position and direction of the electro-acoustic transducer 120 in the bore 111, according to an exemplary embodiment. In FIGS. 4C and 4D, the electro-acoustic transducer 120 includes a coil 122 through which a current flows and a vibrating plate 121 that vibrates according to a force that is interacting with a magnet of the bore 111.

According to FIG. 4C, the electro-acoustic transducer 120 may be positioned so that the vibration direction 28, i.e., in left and right directions in FIG. 4C, of the vibrating plate 121 and the direction 30 of a magnetic flux are parallel to each other. That is, the electro-acoustic transducer 120 may be positioned so that the direction of a magnetic field generated by a current that flows through the coil 122 and the direction of a magnetic field generated by a magnet are parallel to each other.

Although a described-above acoustic signal is generated when the vibration direction of the electro-acoustic transducer 120 and the direction of the magnetic field generated by the magnet of the MRI apparatus 110 are parallel to each other, the two directions are not limited to being parallel to each other. In other words, as long as the two directions described above are not perpendicular to each other, the electro-acoustic transducer 120 may generate an acoustic signal by vibrating due to a force interacting with the magnet. That is, the electro-acoustic transducer 120 may be positioned so that the vibrating direction thereof is not perpendicular to the direction of the magnetic field.

According to FIG. 4D, the electro-acoustic transducer 120 may be positioned so that a central axis 123 that is formed by the coil 122 and the direction 30 in which a magnet flux is focused are parallel to each other. That is, the electro-acoustic transducer 120 may be positioned so that the direction of a magnetic field generated by a current that flows through the coil 122 and the direction of a magnetic field of the magnet are parallel to each other. However, an exemplary embodiment is not limited to the case where the direction of a magnetic field of the electro-acoustic transducer 120 and the direction of a magnetic field of the magnet of the MRI apparatus 110 are parallel to each other. That is, the electro-acoustic transducer 120 may generate an acoustic signal by being positioned so that the direction of the magnetic field of the electro-acoustic transducer 120 and the direction of a magnetic field of the magnet of the MRI apparatus 110 are not perpendicular to each other.

As described with reference to FIG. 4, the electro-acoustic transducer 120 may vibrate according to a force that is interacting with the magnet of the MRI apparatus 110 by being positioned in the bore 111, thereby generating an acoustic signal. In FIG. 4, the case where the electro-acoustic transducer 120 is positioned in the bore 111 is described. However, the above description may be the same when the electro-acoustic transducer 120 is positioned outside of the bore 111 and the magnetic field of the MRI magnet is distributed.

That is, when the electro-acoustic transducer 120 is positioned outside of the bore 111, an attractive force or a repulsive force is generated between the electro-acoustic transducer 120 and the magnet of the MRI apparatus 110, and the vibrating plate 121 vibrates according to an interacting force. In other words, although the intensity of the interacting force may vary, the vibrating plate 121 may still vibrate.

FIGS. 5A and 5B are perspective views of the electro-acoustic transducer 120 and the MRI apparatus 110 according to an exemplary embodiment. In FIG. 5A, the magnet of the MRI apparatus 110 is a superconducting magnet, and in FIG. 5B, the magnet of the MRI apparatus 110 is a permanent magnet. The magnet of FIG. 5B may be of an open type.

According to FIG. 5A, the electro-acoustic transducer 120 may be positioned outside or inside of the bore 111, as described with reference to FIG. 4, and thus, the repeated description will be omitted. The electro-acoustic transducer 120 in FIG. 5B may be positioned within a gantry of the MRI apparatus 110. That is, in a permanent magnet MRI apparatus 110 that are also referred to as an open type MRI apparatus, the electro-acoustic transducer 120 may be positioned in a magnetic field formed by an upper magnet 151 and a lower magnet 152.

The electro-acoustic transducer 120 in FIG. 5B may be positioned so that the vibration direction 26, i.e., the up and down direction in FIG. 5B, of the vibrating plate 121 is parallel to the direction 30 of a magnet flux formed by the upper magnet 151 and the lower magnet 152. The electro-acoustic transducer 120 may be positioned so that the central axis 123 of the coil 122 is parallel to the direction of a magnet flux formed by the upper magnet 151 and the lower magnet 152. Accordingly, the electro-acoustic transducer 120 FIG. 5B generates an acoustic signal by vibrating vertically in the direction of a magnet flux. The electro-acoustic transducer 120 in FIG. 5A may be positioned so that the direction of a magnet flux is not perpendicular to the vibration direction.

FIGS. 6A, 6B, 6C, and 6D show control of an intensity of a current input to the electro-acoustic transducer 120 according to the horizontal position of the electro-acoustic transducer 120, according to an exemplary embodiment.

FIG. 6A shows the intensities of a magnetic field inside and outside of the bore 111. FIGS. 6B through 6D show movements of the cradle 112 when the electro-acoustic transducer 120 is provided on a headset.

More specifically, in FIG. 6B, the head of the patient 113 is positioned at a center portion 620 of the bore 111, in FIG. 6C, the waist of the patient 113 is positioned at the center portion 620 of the bore 111, and in FIG. 6D, the knees of the patient 113 are positioned at the center portion 620 of the bore 111. That is, in drawings FIGS. 6B through 6D, the horizontal position of the cradle 112 is controlled so that the ROI of the patient 113 is positioned at the center portion 620 of the bore 111.

Hereinafter, the control of the intensity of a current input to the electro-acoustic transducer 120 according to the horizontal position of the electro-acoustic transducer 120 as depicted in FIGS. 6B through 6D according to an exemplary embodiment will be described.

In FIG. 6A, the intensity of a magnetic field generated by a magnet of the bore 111 varies according to positions inside and outside of the bore 111. A graph 610 depicted in FIG. 6A shows the variations of the intensity of the magnetic field. In FIG. 6A, when moving in a right-hand direction from an entrance 618 of the bore 111, first, a region 111b is a region where the magnet flux is most densely focused (that is, the magnetic intensity is the strongest in this region). Also, a magnetic field having a relatively uniform intensity is formed in the region 111b.

Next, the intensity of the magnetic field is reduced when moving from the region 111b towards a region 111c in the bore 111. That is, unlike a theoretical magnet, a real magnet has a fixed length. Therefore, the intensity of the magnetic field in the bore 111 is weaker near the end of the bore 111. However, as depicted FIG. 6A, the bore 111 may include a predetermined region where the intensity of the magnetic field increases near an end of the magnet (between the region 111c and a region 111d).

Finally, the intensity of the magnetic field formed by the magnet is lower in the region 111d outside of the bore 111 than inside the bore 111, and the intensity becomes lower in a direction farther from the magnet of the bore 111. Accordingly, at a location at a predetermined distance from the magnet of the bore 111, a magnetic field having intensity not sufficient enough for the electro-acoustic transducer 120 may be detected.

In FIG. 6B, when the cradle 112 is moved so that the head of the patient 113 is positioned at the center portion 620 of the bore 111, the electro-acoustic transducer 120 is positioned in the region 111b of the bore 111. That is, the electro-acoustic transducer 120 may be positioned at a position where the intensity of the magnetic field is the strongest within the bore 111. The controller 130 may control the intensity of an input current so that an acoustic signal generated from the electro-acoustic transducer 120 has a predetermined intensity (not to be too loud or weak) by using the intensity of the magnetic field of the region 111b. The controller 130 may control the intensity of the input current by using the intensity of the magnetic field in the region 111b stored in advance in the storage 131. As described above with reference to FIG. 2, the storage 131 may store in advance information about the experimentally obtained intensity of the magnetic field and the intensity of an input current.

In FIG. 6C, when the cradle 112 is moved so that the waist of the patient 113 is positioned at the center portion 620 of the bore 111, the electro-acoustic transducer 120 is positioned in region 111c of the bore 111. That is, the electro-acoustic transducer 120 of the MRI apparatus 110 is moved inside the bore 111 further than the position shown in FIG. 6B. As the electro-acoustic transducer 120 is moved, the intensity of the magnetic field at a point (for example, the region 111c in FIG. 6A) where the electro-acoustic transducer 120 is positioned is changed. Accordingly, the controller 130 may control the intensity of the input current so that electro-acoustic transducer 120 generates an acoustic signal having the same intensity as the acoustic signal generated at the position in FIG. 6B.

For example, as described with reference to of FIG. 6A, since the intensity of the magnetic field varies according to the position in the bore 111, the electro-acoustic transducer 120 at the position in FIG. 6C is affected in a smaller degree than at the position in FIG. 6B, by the intensity of the magnetic field. Therefore, the controller 130 may control to increase an input current in order to generate a constant intensity acoustic signal although the intensity of the external magnetic field is changed.

In FIG. 6D, when the cradle 112 is moved so that the knees of the patient 113 are positioned at the center portion 620 of the bore 111, the electro-acoustic transducer 120 is positioned in the region 111d outside of the bore 111. The controller 130 may control to increase an input current to the electro-acoustic transducer 120 as the electro-acoustic transducer 120 is moved further than the position shown in FIG. 6C. That is, the controller 130 may control the intensity of the input current according to the intensity of the magnetic field in the region 111d where the electro-acoustic transducer 120 is positioned.

In FIGS. 6B through 6D, the imaging process is described sequentially, with respect to the regions of the patient, but an exemplary embodiment is not limited thereto. The imaging sequence of the patient 113 is not limited to the order of head-waist-knees. The controller 130 may control the intensity of the input current by using information about the relationship between the horizontal position and the intensity of input current stored in advance whenever the horizontal position of the electro-acoustic transducer 120 changes.

The same descriptions made above with reference to FIGS. 6B through 6D in relation to the electro-acoustic transducer 120 may apply to the acoustic output device 126 that includes the electro-acoustic transducer 120 described with reference to FIG. 3 (or that includes the electro-acoustic transducer 120 and the controller 130).

According to an exemplary embodiment, the controller 130 may control the intensity of the current input to the electro-acoustic transducer 120 by detecting a moving distance of the cradle 112 into the magnetic field. That is, the controller 130 may use the moving distance of the cradle 112 in order to detect the horizontal position of the electro-acoustic transducer 120.

Also, as another example, the controller 130 may detect the horizontal position of the electro-acoustic transducer 120 by using the intensity of the magnetic field detected by the detector 132 at a predetermined location. That is, when the detector 132 provided in the acoustic output device 126, the detector 132 may detect the intensity of the magnetic field that varies according to the movement of the cradle 112. Accordingly, the controller 130 may control the intensity of the acoustic signal by controlling the intensity of the current input to the electro-acoustic transducer 120 in response to the intensity of the varying magnetic field.

According to an exemplary embodiment, as described with reference to FIG. 2, the controller 130 may block the input current by controlling the intensity of the input current. That is, the controller 130 may control the electro-acoustic transducer 120 not to generate an acoustic signal by blocking the current input to the electro-acoustic transducer 120. According to an exemplary embodiment, since the electro-acoustic transducer 120 is operated according to the magnetic field around the electro-acoustic transducer 120, the durability of the electro-acoustic transducer 120 may be improved.

That is, the cradle 112 may be moved to a position where the intensity of the magnetic field of the electro-acoustic transducer 120 at a horizontal position is not strong enough for the electro-acoustic transducer 120 to generate an acoustic signal. The controller 130 may block a current from being input to the electro-acoustic transducer 120 when the horizontal position of the electro-acoustic transducer 120 outside of the range of a horizontal position determined in advance (the range of the horizontal position that is sufficient enough to generate an acoustic signal).

The controller 130 may block an input current based not only on the horizontal position of the electro-acoustic transducer 120 but also on the intensity of a magnetic field that is below a critical value. That is, when the detector 132 together with the electro-acoustic transducer 120 is provided on the acoustic output device 126 such as a headset, the controller 130 may block the input current if the intensity of the magnetic field detected at the position of the headset falls below a critical value. According to an exemplary embodiment, when the headset is not worn by the patient 113 but is kept at a separated location, the controller 130 may block the input current based on the intensity of the magnetic field, thereby increasing the durability of the electro-acoustic transducer 120.

Figure 7B:
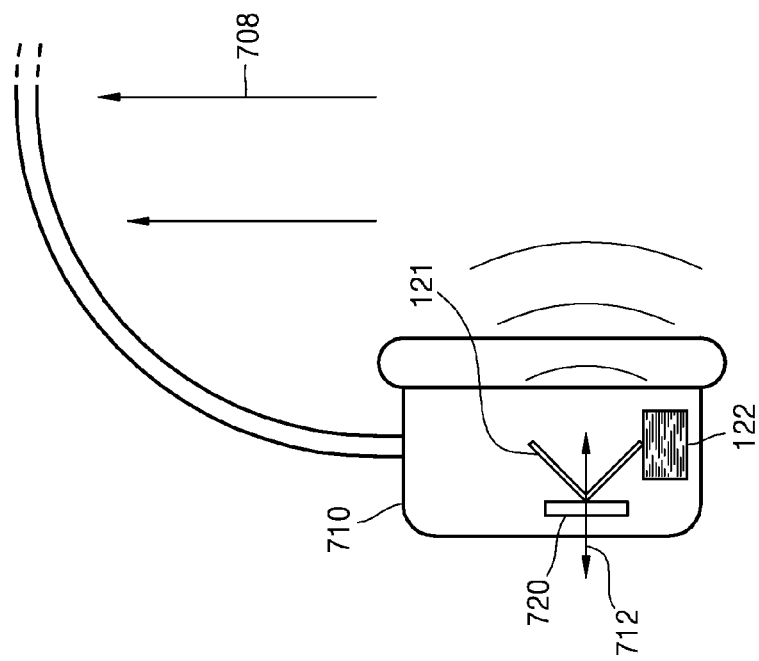
FIGS. 7A and 7B show a headset according to an exemplary embodiment.
Figure 7A:
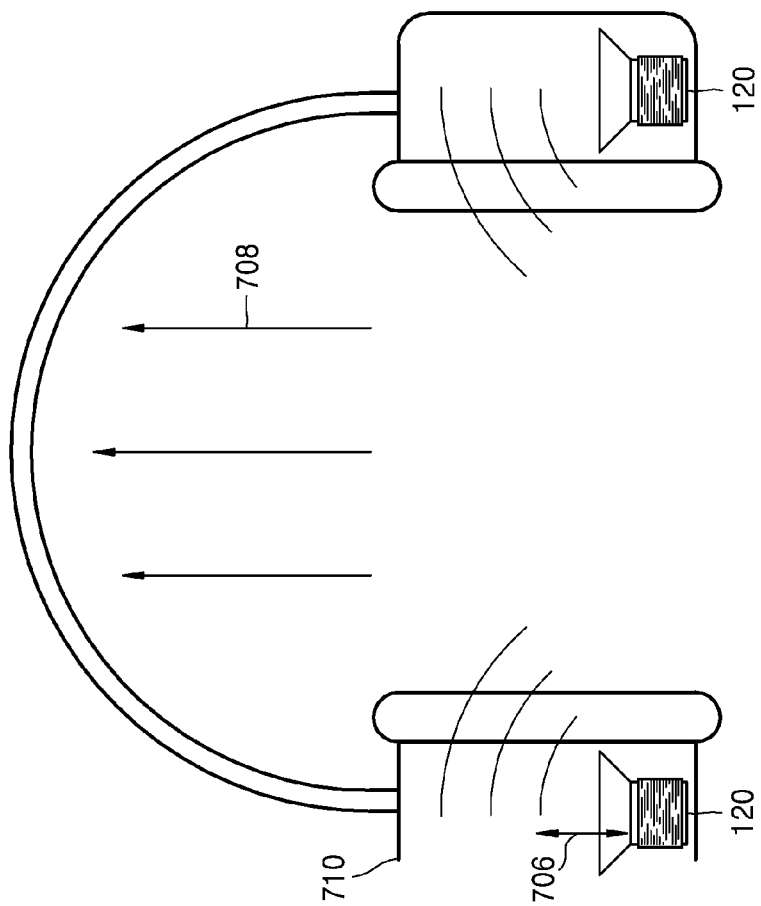

FIGS. 7A and 7B show an acoustic output device 710 according to an exemplary embodiment.

In FIG. 7A, the electro-acoustic transducer 120 is provided in a headset as the acoustic output device 710. As depicted in FIG. 7A, the electro-acoustic transducer 120 may generate an acoustic signal by using a magnetic field generated in a vertical direction 708 of the MRI apparatus 110. That is, the acoustic output device 710 may include the electro-acoustic transducer 120 that is positioned such that the vibrating direction 706 of the vibrating plate 121 or the direction of the central axis 123 of the coil 122 is not perpendicular to the direction of the magnetic field of the MRI apparatus 110. The acoustic output device 710 may include the controller 130 that controls the intensity of an input current according to the horizontal position of the electro-acoustic transducer 120 in the bore 111. However, an exemplary embodiment is not limited thereto, that is, the controller 130 may be a separate element located outside of the acoustic output device 710.

FIG. 7B shows the acoustic output device 710 in which the vibrating plate 121 of the electro-acoustic transducer 120 vibrates in a direction 712 perpendicular to the direction 708 of the magnetic field, according to an exemplary embodiment. In FIG. 7A, the vibrating plate 121 of the acoustic output device 710 vibrates, up and down, and an acoustic signal (a sound wave) generated in the acoustic output device 710 is transmitted to the patient 113 by being reflected by a side surface of the acoustic output device 710.

However, in the acoustic output device 710 in FIG. 7B, the vibrating plate 121 vibrates left and right laterally. That is, the acoustic output device 710 depicted in FIG. 7B, according to an exemplary embodiment may include a direction conversion unit 720 that is combined with the vibrating plate 121 to vibrate the vibrating plate 121 in a direction perpendicular to a direction of the magnetic field generated by the coil 122 (that is, a direction of the magnetic field of the MRI apparatus 110).

According to an exemplary embodiment, an acoustic signal generated from the acoustic output device 710 is not transmitted by reflection but is directly transmitted to the patient 113. Therefore, the acoustic signal may have a better sound quality.

Figure 8A:
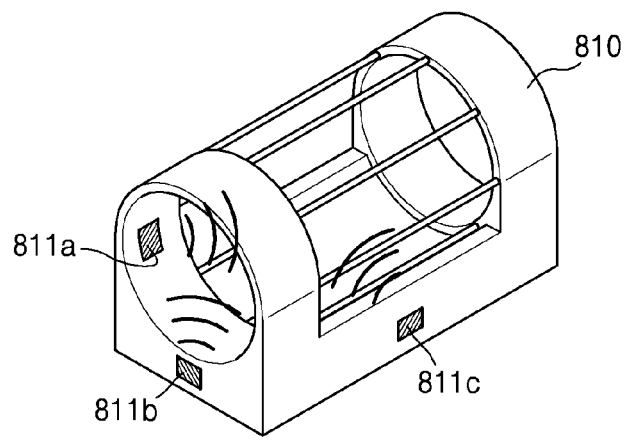
FIGS. 8A, 8B, 8C, 8D, and 8E show positioning of an electro-acoustic transducer according to an exemplary embodiment.
Figure 8B:
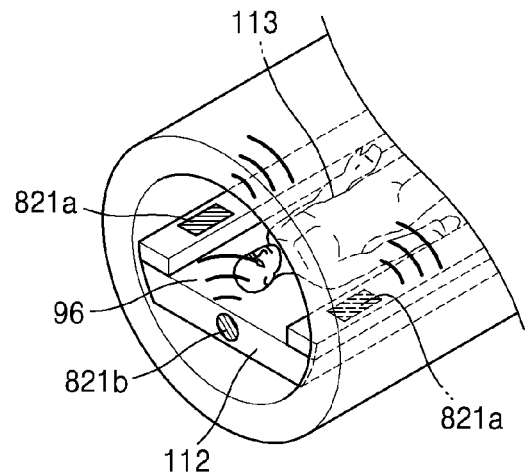
Figure 8C:
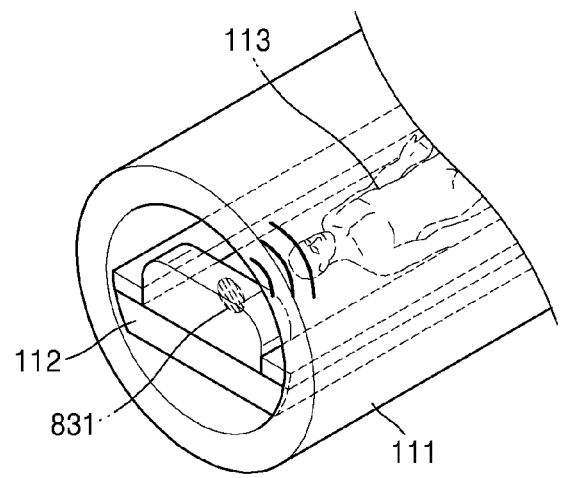

FIGS. 8A, 8B, 8C, 8D, and 8E show positioning of the electro-acoustic transducer 120 according to an exemplary embodiment. FIG. 8A shows the electro-acoustic transducer 120 mounted on a head RF coil 810 according to an exemplary embodiment. FIG. 8B and FIG. 8C respectively show the electro-acoustic transducer 120 positioned on a head portion 96 of the cradle 112, according to an exemplary embodiment.

In FIG. 8A, the electro-acoustic transducer 120 may be positioned at various locations such as on an inner sidewall 811a, an outer sidewall 811b, and end surface 811c of the head RF coil 810. As described above, the electro-acoustic transducer 120 may be positioned so that the vibrating direction of the vibrating plate 121 or the direction of the central axis 123 of the coil 122 is not perpendicular to the direction of the magnetic field of the MRI apparatus 110.

The electro-acoustic transducer 120 provided at each position of the head RF coil 810, may control the direction of transmitting an acoustic signal to the patient 113 by using the direction conversion unit 720, as described with reference to FIG. 7B.

In FIGS. 8B and 8C, the electro-acoustic transducer 120 may be positioned in a head portion 96 of the cradle 112 where the patient 113 is positioned. That is, the electro-acoustic transducer 120 may be provided at a predetermined position (that is, in the head portion 96) near the head of the patient 113 so that an acoustic signal is effectively transmitted to patient 113 lying on the cradle 112.

As depicted in FIG. 8B, the electro-acoustic transducer 120 may be positioned on both sides 821a of the cradle 112 or on an upper side 821*b* of the cradle 112. Also, as depicted in FIG. 8C, the electro-acoustic transducer 120 may generate an acoustic signal to be transmitted to the patient 113 by being positioned on a side 831 of the head portion 96 of the cradle 112.

Figure 8D:
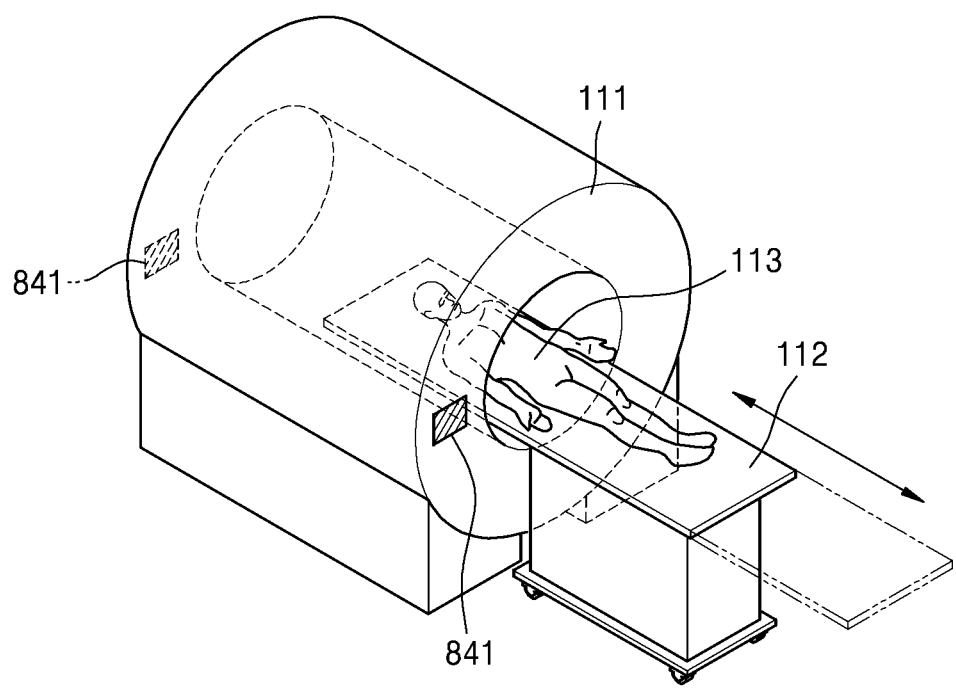
Figure 8E:
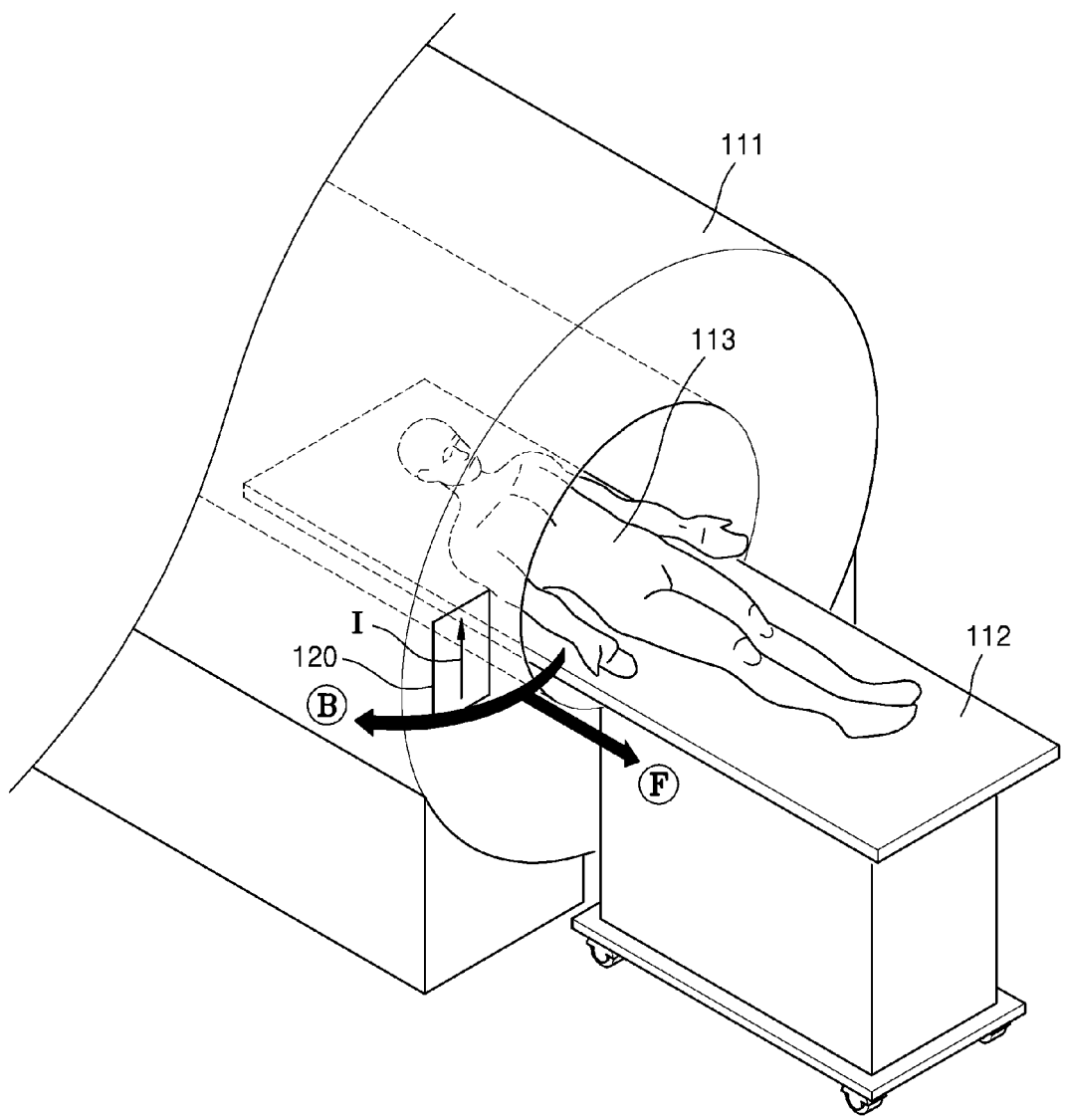

In the embodiment depicted in FIGS. 8D and 8E, the electro-acoustic transducer 120 may be located outside of the bore 111. That is, the electro-acoustic transducer 120 may be located outside of the bore 111 so that an acoustic signal is effectively transmitted to the patient 113 or the user of the MRI apparatus 110, who locates outside of the bore 111.

A magnetic field that may be generated by a magnet of the MRI apparatus 110 may be generated as the arrows in FIG. 4B. As depicted in FIG. 4B, the magnetic field in the bore 111 may be generated in a horizontal direction, and the magnetic field outside of the bore 111 may bend along an outer surface of the bore 111. In the MRI acoustic system 100 according to an exemplary embodiment, the electro-acoustic transducer 120 may be disposed on a portion of the bending magnetic field.

As depicted in FIG. 8D, the electro-acoustic transducer 120 may be located on at least one of a top surface and a bottom surface 841 of the bore 111 having a column shape. The electro-acoustic transducer 120 may include a coil through which a current flows for generating an attractive force or a repulsive force with respect to a magnetic field that is generated by a magnet included in the bore 111 and a vibrating plate that vibrates in response to the attractive force or the repulsive force. As described above, the electro-acoustic transducer 120 may be located outside of the bore 111 so that the vibration direction of the vibrating plate or the direction of a center axis of the coil is not perpendicular to the direction of the magnetic field. For example, the electro-acoustic transducer 120 may be located outside of the bore 111 so that the direction of a current that flows in the coil is not parallel to the direction of the magnetic field that is generated by the magnet.

As depicted in FIG. 8E, the electro-acoustic transducer 120 may be located on a bottom surface of the bore 111 having a column shape. In FIG. 8E, when a current flows in a direction indicated by "I" with respect to a magnetic field indicated by "B", the vibrating plate of the electro-acoustic transducer 120 receives a Lorentz force in a direction indicated by "F". In response to the Lorentz force, the vibrating plate of the electro-acoustic transducer 120 vibrates, and thus, an acoustic signal may be generated by the vibration of the vibrating plate.

As depicted in FIG. 8E, the electro-acoustic transducer 120 may be located on a bottom surface of the bore 111 so that the direction of the current I that flows along the coil is perpendicular to the magnetic field B that is generated by a magnet. At this point, the vibrating plate of the electro-acoustic transducer 120 may be configured to vibrate in a direction parallel to the direction of moving the cradle where the patient 113 is positioned in order to accommodate the patient 113 in the image-taking space of the bore 111.

In FIGS. 8A through 8E, examples of positions of the electro-acoustic transducer 120 are shown. However, the MRI acoustic system 100 may include the electro-acoustic transducer 120 located at various positions and operated by various methods besides the positions and methods depicted and described above.

Figure 9A:
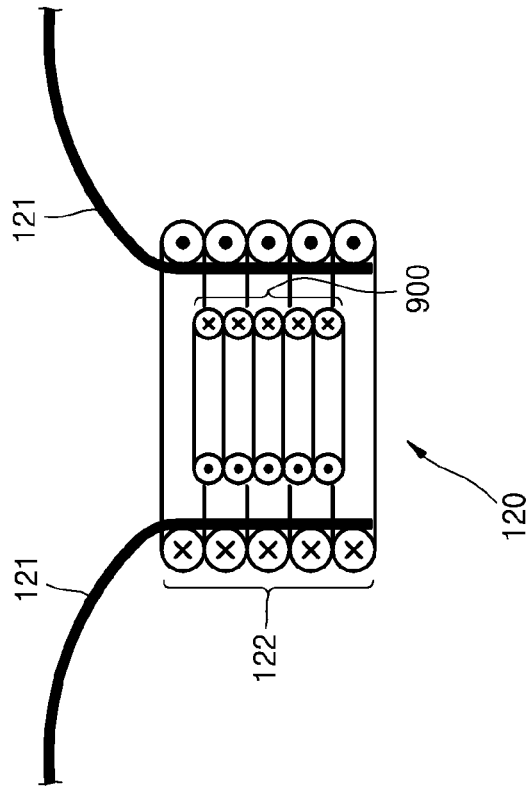
FIGS. 9A and 9B show a structure of an electro-acoustic transducer according to an exemplary embodiment.
Figure 9B:
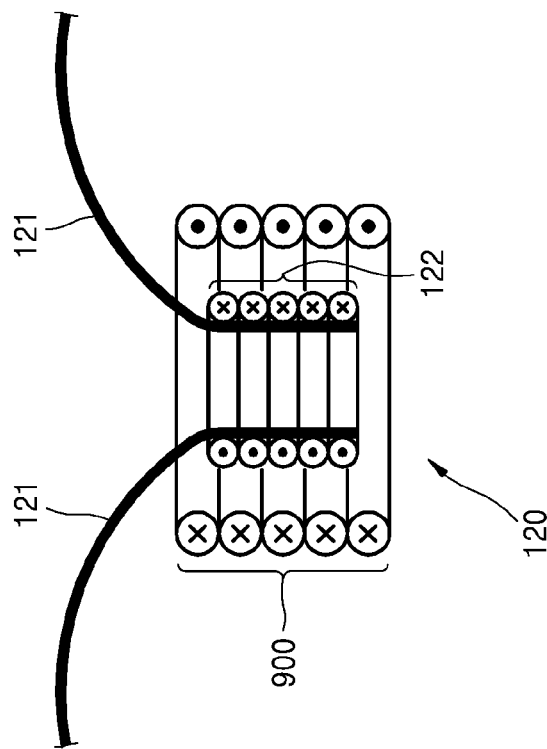

FIGS. 9A and 9B show the structure of an electro-acoustic transducer 120 that includes a shield coil 900 according to an exemplary embodiment. The electro-acoustic transducer 120 depicted in FIGS. 9A and 9B includes a magnet of an MRI apparatus 110, a coil 122 through which a current that generates an attractive force or a repulsive force flows, a vibrating plate 121 that is combined with the coil 122 to vibrate according to a force interacting with the MRI apparatus 110, and the shield coil 900 that shields the magnetic field generated by the coil 122.

Although not shown in FIGS. 9A and 9B, the electro-acoustic transducer 120 according to an exemplary embodiment may further include elements, such as a damper that supports a vertical movement of the coil 122 and the vibrating plate 121, a bobbin combined with the coil 122, and a lead wire that connects the coil 122 to an electrical signal input terminal.

Hereinafter, the shield coil 900 depicted in FIGS. 9A and 9B will be described in detail. As described with reference to FIG. 4, when a current flows through the coil 122 of the electro-acoustic transducer 120, a magnetic field is generated. A magnetic field (different from the magnetic field in the bore 111) generated by a current that flows through the coil 122 of the electro-acoustic transducer 120 is focused on the center portion of the coil 122. A magnetic field generated by a current that flows through the coil 122 is smaller than that of the bore 111 of the MRI apparatus 110, but may affect a main magnetic field of the MRI apparatus 110 for obtaining an MRI image. Accordingly, there is a need to offset or minimize a magnetic field generated by a current that flows in the coil 122.

The shield coil 900 depicted in FIGS. 9A and 9B has the same central axis as the central axis 123 of the coil 122, and may be positioned inside or outside of the coil 122. In FIG. 9A, as an example, the shield coil 900 is positioned outside of the coil 122, and in FIG. 9B, the shield coil 900 is positioned inside the coil 122. In FIGS. 9A and 9B, the thicknesses of the coil 122 and the shield coil 900 are different from each other for convenience of explanation and understanding. Nevertheless, the thicknesses of the coil 122 and the shield coil 900 may be the same or different.

The direction of a current (hereinafter, a second current) that flows through the shield coil 900 and the direction of a current (hereinafter a first current) that flows through the coil 122 are opposite to each other. That is, the direction of a magnetic field (a direction according to the Ampere's Rule (the Right Hand Screw Rule)) generated by the shield coil 900 is opposite to the direction of a magnetic field generated by the coil 122, and thus, the magnetic field focused on the center portion of the coil 122 may be offset by the magnetic field generated by the shield coil 900.

According to an exemplary embodiment, the intensities of the first and second currents may be controlled by the controller 130. That is, the controller 130 may control the intensity of the first current to be different from that of the second current when controlling the intensity of a current input to the electro-acoustic transducer 120.

More specifically, the shield coil 900 depicted in FIG. 9A has a length greater than the coil 122, and thus, if the intensities of the first current and the second current are equal, the intensity of a magnetic field generated by the shield coil 900 is greater than that of the magnetic field generated by the coil 122. Accordingly, the controller 130 may control the intensity of the second current that flows through the shield coil 900 to be smaller than that of the first current that flows through the coil 122 so that the intensities of the magnetic fields generated by the shield coil 900 and the coil 122 are equal.

On the contrary, the shield coil 900 depicted in FIG. 9B has a length smaller than that of the coil 122. Accordingly, the controller 130 may control the intensity of the first current that flows through the coil 122 to be smaller than that of the second current that flows through the shield coil 900 by controlling the intensity of the current input to the electro-acoustic transducer 120.

The magnetic field generated by the coil 122 may be offset or minimized by controlling the numbers of turns of the coil 122 and the shield coil 900. That is, for example, in FIG. 9A, the intensity of the magnetic field generated by the coil 122 may be increased by winding the coil 122 by a greater number of turns than the shield coil 900. In this way, the magnetic field may be offset by controlling the numbers of windings of the shield coil 900 and the coil 122.

FIGS. 10A and 10B show the electro-acoustic transducer 120 that includes fixing units 1010 and 1020 according to an exemplary embodiment. In FIGS. 10A and 10B, the shield coil 900 is connected to the fixing units 1010 and 1020.

The fixing units 1010 and 1020 depicted in of FIGS. 10A and 10B fix the shield coil 900 by being connected thereto. That is, the fixing units 1010 and 1020 may fix the shield coil 900 so that the shield coil 900 does not generate an attractive force or a repulsive force with the magnet of the MRI apparatus 110. If the shield coil 900 is not fixed, the shield coil 900 may move by a force interacting with the magnet of the MRI apparatus 110, and thus, noise may be included in an acoustic signal generated by the coil 122 combined with the vibrating plate 121. Although not shown in FIGS. 10A and 10B, the fixing units 1010 and 1020 may fix the shield coil 900 by being combined with a frame of the electro-acoustic transducer 120.

The fixing unit 1010 depicted in FIG. 10A may fix the shield coil 900 by being combined with the shield coil 900 that is located outside of the coil 122. On the contrary, the fixing unit 1020 depicted in FIG. 10B fix the shield coil 900 by being combined with the shield coil 900 located inside the coil 122. The fixing units 1010 and 1020 shown in FIGS. 10A and 10B are only examples to fix the shield coil 900, and thus, the shield coil 900 may be fixed on the frame of the electro-acoustic transducer 120 through various methods, for example, by using an elastic member such as a spring.

Figure 11:
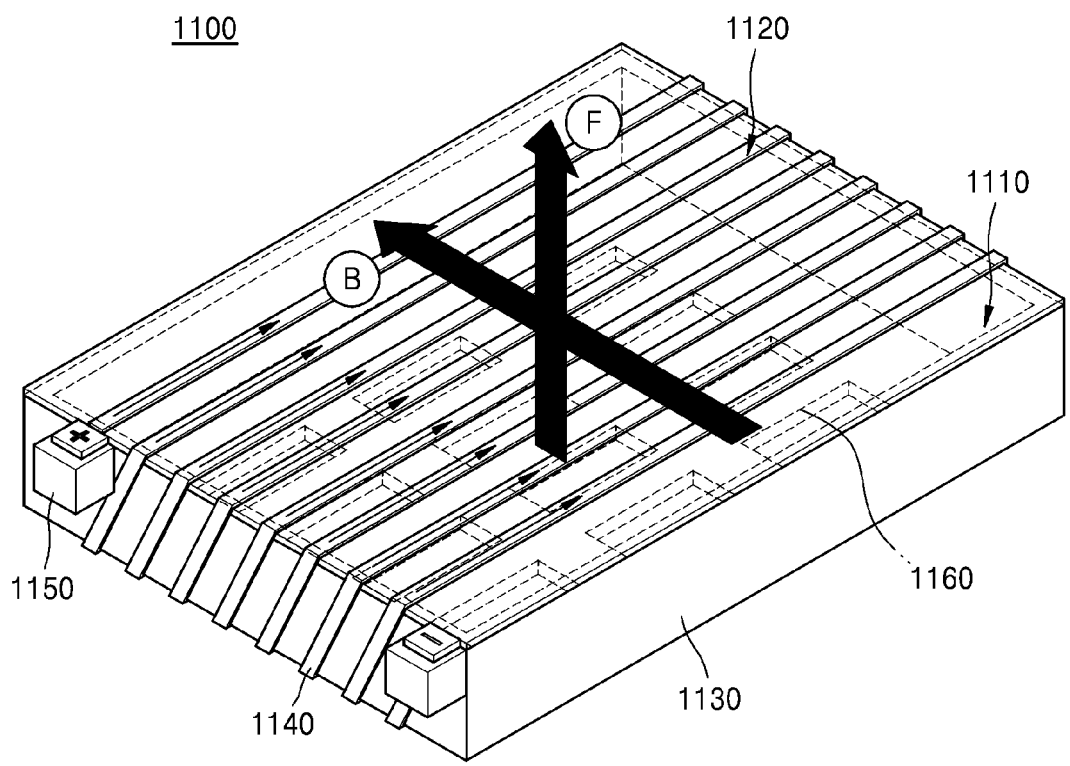
FIG. 11 is a perspective view showing a structure of an electro-acoustic transducer according to an exemplary embodiment.

FIG. 11 is a perspective view showing the structure of a case type electro-acoustic transducer 1100 according to an exemplary embodiment. In FIG. 11, the electro-acoustic transducer 1100 is of a different type from the electro-acoustic transducer 120 described above.

The electro-acoustic transducer 1100 may include a vibrating unit 1110 that vibrates according to a Lorentz force formed by an MRI apparatus 110, a supporting unit 1130 that fixes both edges of the vibrating unit 1110, and a coil through which a current that experiences the Lorentz force flows. The structure of the electro-acoustic transducer 1100 depicted in FIG. 11 is an example, and thus, the electro-acoustic transducer 1100 that includes the vibrating unit 1110, the supporting unit 1130, and the coil may further include structure besides the structure depicted in FIG. 11.

The coil through which a current flows in the electro-acoustic transducer 1100 depicted in FIG. 11 may include at least one first coil 1120 disposed on the vibrating unit 1110 and at least one second coil 1140 fixed on the supporting unit 1130. That is, when a current is input through an input terminal 1150 depicted in FIG. 11, the current may flow through the first coil on the vibrating unit 1110, and may flow through the second coil 1140 fixed on the supporting unit 1130 at one end of the vibrating unit 1110. Next, the current that flows through the second coil 1140 that is fixed on the supporting unit 1130 flows along a lower end surface of the electro-acoustic transducer 1100, and may flow again through the first coil 1120 at the other end of the vibrating unit 1110.

Also, according to the electro-acoustic transducer 1100 depicted in FIG. 11, the first coil 1120 and the second coil 1140 are parallel to each other, and the current flows therethrough in opposite directions to each other. That is, since the current flows continuously through the first coil 1120 and the second coil 1140, the direction of the current that flows in the vibrating unit 1110 and the direction of the current that flows in the lower end surface of the supporting unit 1130 are opposite to each other. According to the structure described above, a magnetic field outside of an ideal solenoid coil is 0, and thus, a magnetic field generated outside of the electro-acoustic transducer 1100 depicted in FIG. 11 may be minimized.

In the structure of the electro-acoustic transducer 1100 according to an exemplary embodiment, the effect of a magnetic field generated by a current that flows through the coil of the electro-acoustic transducer 1100 to a magnetic field of the MRI apparatus 110 may be minimized.

The vibrating unit 1110 of the electro-acoustic transducer 1100 may be realized in various ways. That is, the vibrating unit 1110 may include a film type vibrating plate or an elastic member vibrating plate. In addition, the vibrating unit 1110 may be realized in various configurations that may vibrate according to the Lorentz force.

When the electro-acoustic transducer 1100 according to an exemplary embodiment operates, the vibrating unit 1110 and the first coil 1120 vibrate according to the Lorentz force, but the second coil 1140 is fixed on the supporting unit 1130. Accordingly, the first coil 1120 and the second coil 1140 of the electro-acoustic transducer 1100 may be separately attached to or formed on the vibrating unit 1110 and the supporting unit 1130. That is, each of the first coil 1120 and the second coil 1140 may be combined after being formed as separate parts.

For example, the first coil 1120 disposed in advance on the vibrating unit 1110 and the second coil 1140 fixed on the supporting unit 1130 may be connected by a well-known suitable technique in the art, such as bonding or assembling the vibrating unit 1110 and the supporting unit 1130. Accordingly, the combined first coil 1120 and the second coil 1140 may form a coil that surrounds the vibrating unit 1110 and the supporting unit 1130 of the electro-acoustic transducer 1100.

However, the electro-acoustic transducer 1100 may be formed by disposing a single coil along a surface of the supporting unit 1130 and the vibrating unit 1110 that are combined in advance. That is, the coil of the electro-acoustic transducer 1100 is not combined after the first coil 1120 and the second coil 1140 are separately formed, but in a coil formed in advance, parts that are connected to the vibrating unit 1110 and the supporting unit 1130 respectively may be the first coil 1120 and the second coil 1140.

Hereinafter, a process of operating the electro-acoustic transducer 1100 depicted in FIG. 11 according to a Lorentz force will be described. A current that flows in a magnetic field receives the Lorentz force, and the direction of the Lorentz force is perpendicular to the direction of the magnetic field according to the Fleming's left-hand rule.

In FIG. 11, a direction of a magnetic field is indicated by "B". When a current flows in the direction indicated by "B", the electro-acoustic transducer 1100 that uses a magnetic field of the MRI apparatus 110 receives a Lorentz force (indicated by "F") in an upper direction, which is perpendicular to the vibrating unit 1110. The vibrating unit 1110 vibrates according to the Lorentz force, and a sound wave generated by the vibration of the vibrating unit 1110 may generate an acoustic signal.

The vibrating unit 1110 may be formed of a nonmagnetic material. According to an exemplary embodiment, the vibrating unit 1110 may be formed of a paramagnet material or a low magnetic material that affects a magnetic field of the MRI apparatus 110 less than a critical value.

When an alternating (AC) current is input to the electro-acoustic transducer 1100, the direction of the Lorentz force that is received by the vibrating unit 1110 varies together with the direction of the current that varies as the direction of the magnetic field is maintained. That is, when a current flows in the direction depicted in FIG. 11, the direction of the Lorentz force is upward, which is perpendicular to the vibrating unit 1110. However, when the current flows in a counter direction, the direction of the Lorentz is downward, which perpendicular to the vibrating unit 1110. The vibrating unit 1110 vibrates according to the Lorentz force and may generate an acoustic signal.

As described above, the electro-acoustic transducer 1100 depicted in FIG. 11 according to an exemplary embodiment may be positioned so that the vibrating unit 1110 is parallel to the direction of a magnet of the MRI apparatus 110 and the current that flows through the first coil 1120 disposed on the vibrating unit 1110 is perpendicular to the direction of the magnetic field. That is, the electro-acoustic transducer 1100 may be positioned in a direction that the current that flows through the first coil 1120 experiences the Lorentz force generated by a magnetic field of the MRI apparatus 110.

The electro-acoustic transducer 1100 receives the Lorentz force the most when a direction of the current is perpendicular to the direction of a magnet field. However, an angle that is formed by the two directions according to the current invention is not limited to 90°. That is, the Lorentz force that is transmitted to the electro-acoustic transducer 1100 from the magnetic field of the MRI apparatus 110 is generated when an angle between the direction of the current and the direction of the magnetic field is not 0° or 180°. Accordingly, the electro-acoustic transducer 1100 may be positioned so that the direction of the current and the direction of the magnetic field are not parallel to each other.

The supporting unit 1130 of the electro-acoustic transducer 1100 may include at least one aperture 1160. The aperture 1160 formed in the supporting unit 1130 may form a path through which an air in the electro-acoustic transducer 1100 is circulated as the vibrating unit 1110 vibrates. In FIG. 11, the aperture 1160 is formed in a bottom of the supporting unit 1130 in a rectangular shape. However, the shape and location of the aperture 1160 according to an exemplary embodiment is not limited thereto. That is, the aperture 1160 may have various shapes, and may be formed not only in the bottom of the supporting unit 1130 but also in a sidewall (that is, a sidewall of the supporting unit 1130 where the coil is not formed) of the supporting unit 1130.

According to an exemplary embodiment described above, the electro-acoustic transducer 1100 that includes the vibrating unit 1110 and the supporting unit 1130 may vibrate according to the Lorentz force that is generated when a current flows through the coil 1120, and thus, may generate an acoustic signal. The electro-acoustic transducer 1100 described above is one case selected for convenience of explanation, and thus, the vibrating unit 1110, the supporting unit 1130, and the coil may be of various types.

Figure 12A:
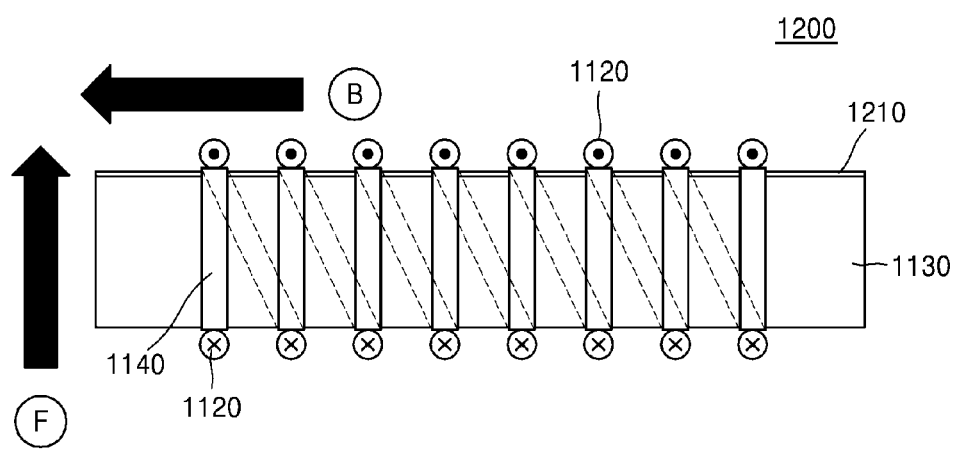
FIGS. 12A and 12B show a structure of an electro-acoustic transducer according to an exemplary embodiment.

FIG. 12A is a lateral view showing a structure of the electro-acoustic transducer 1200 according to an exemplary embodiment. The electro-acoustic transducer 1200 depicted in FIG. 12A is a lateral view of the electro-acoustic transducer 1100 described with reference to FIG. 11, and thus, overlapping descriptions are omitted.

As depicted in FIG. 12A, the electro-acoustic transducer 1200 includes the first coil 1120 formed on the vibrating unit 1210. The first coil 1120 is disposed on the vibrating unit 1210, vibrates together with the vibrating unit 1210 according to the Lorentz force, and is combined with the second coil 1140 so that a current that generate the Lorentz force flows therethrough.

The first coil 1120 according to an exemplary embodiment may include a thin-film coil formed through gilding by printing a predetermined pattern on an insulating film, or formed by etching a copper foil that is bonded to an insulating film.

When the first coil 1120 and the second coil 1140 are formed as one coil and are fixed on the vibrating unit 1210 and the supporting unit 1130, the second coil 1140 may include a thin-film coil like the first coil 1120. However, when the first coil 1120 and the second coil 1140 are formed separately and are combined with each other, the second coil 1140 may be formed through a process different from that of the first coil 1120 and may be disposed on the supporting unit 1130.

Figure 12B:
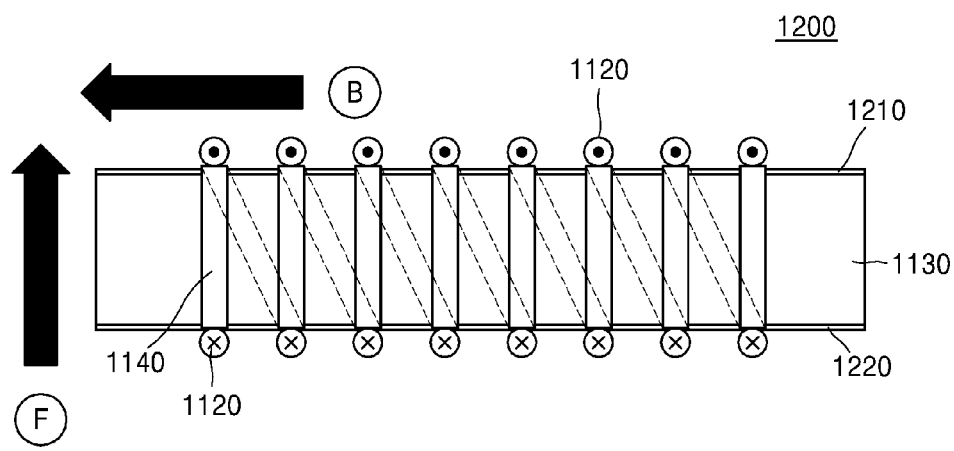

FIG. 12B is a lateral view of the structure of the electro-acoustic transducer 1200 according to an exemplary embodiment. Unlike the electro-acoustic transducer 1100 depicted FIG. 12A, the electro-acoustic transducer 1200 depicted of FIG. 12B may include two vibrating units, that is, a first vibrating unit 1210 and a second vibrating unit 1220 disposed parallel to each other. Both edges of the first vibrating unit 1210 and the second vibrating unit 1220 of the electro-acoustic transducer 1200 depicted in FIG. 12A are respectively combined with the supporting unit 1130.

The first coils 1120 may be respectively disposed on the first vibrating unit 1210 and the second vibrating unit 1220. The description of the first vibrating unit 1210 is the same as the descriptions made with reference to FIG. 11 and FIG. 12A, and the first coil 1120 may also be disposed on the second vibrating unit 1220 (on a surface facing outside of the electro-acoustic transducer 1200). The first coils 1120 disposed on the first vibrating unit 1210 and the second vibrating unit 1220 are connected to the second coil 1140 provided on the supporting unit 1130 to receive the Lorentz force while a current flows therethrough.

According to an exemplary embodiment, in the electro-acoustic transducer 1200 depicted FIG. 12B, when the first vibrating unit 1210 vibrates in an upward direction, the second vibrating unit 1220 vibrates in a downward direction, that is, the first vibrating unit 1210 and the second vibrating unit 1220 may generate an acoustic signal having the same phase by vibrating in opposite directions. In the electro-acoustic transducer 1200 according to an exemplary embodiment depicted in FIG. 12B, apertures may be formed in a side surface of the supporting unit 1130.

Figure 13:
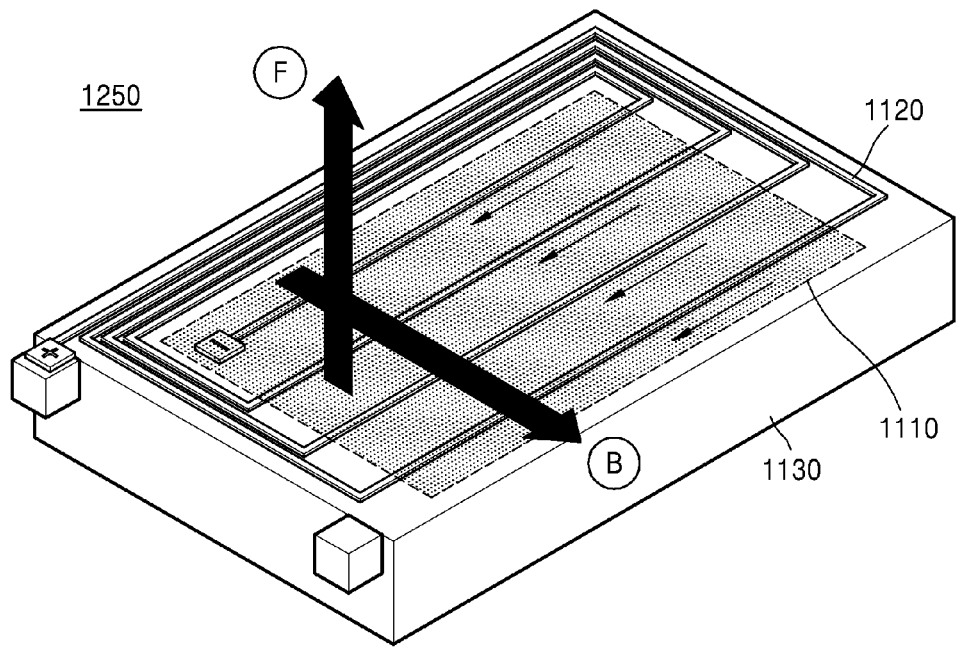
FIG. 13 is a perspective view showing a structure of an electro-acoustic transducer according to an exemplary embodiment.

FIG. 13 is a perspective view showing a structure of an electro-acoustic transducer 1250 according to an exemplary embodiment. The electro-acoustic transducer 1250 depicted in FIG. 13 includes a vibrating unit 1110, a first coil 1120, and a supporting unit 1130. That is, the electro-acoustic transducer 1250 depicted in FIG. 13 has a structure that does not include the second coil 1140 fixed on the supporting unit 1130.

The electro-acoustic transducer 1250 is operated as similarly to the operation described with reference to FIG. 11. That is, a current that flows in a direction indicated by arrows in the first coil 1120 receives the Lorentz force in a direction indicated by "F" in a magnetic field in a direction indicated by "B" in FIG. 13. Accordingly, the vibrating unit 1110 on which the first coil 1120 is disposed vibrates according to the Lorentz force and generates an acoustic signal. At least both edges of the vibrating unit 1110 are fixed by combining them with the supporting unit 1130.

The first coil 1120 is disposed on the vibrating unit 1110 by forming at least one repeating pattern. That is, as depicted in FIG. 13, the first coil 1120 may be disposed by forming a repeating pattern having a rectangular shape.

According to an exemplary embodiment, several of the first coils 1120 may be disposed so that the position of the center portion of the repeating pattern is biased on a side of the first coils 1120. That is, in FIG. 13 as an example, the first coils 1120 may be disposed to receive the Lorentz force in the same direction by disposing some portions of the first coils 1120 that coincide with the direction of a current (the direction of the arrows indicated along the first coils 1120) on the vibrating unit 1110. In other words, a portion of the first coils 1120 through which a current flow in a predetermined direction may be disposed to be located on a predetermined region (for example, on a central region) of the vibrating unit 1110.

A portion of the first coils 1120 besides the portion indicated by arrows in FIG. 13, that is, a portion of the first coils 1120 through which a current flows in a direction in which a force indicated by "F" is not received may be located in an outer region of the vibrating unit 1110. Accordingly, the first coils 1120 that are disposed in an outer region of the vibrating unit 1110 may be disposed on a portion of the vibrating unit 1110 that is fixed on the supporting unit 1130. As a result, the first coils that receive the Lorentz force in a constant direction according to the vibrating unit 1110 may generate an acoustic signal by vibrating in the same direction.

Figure 14:
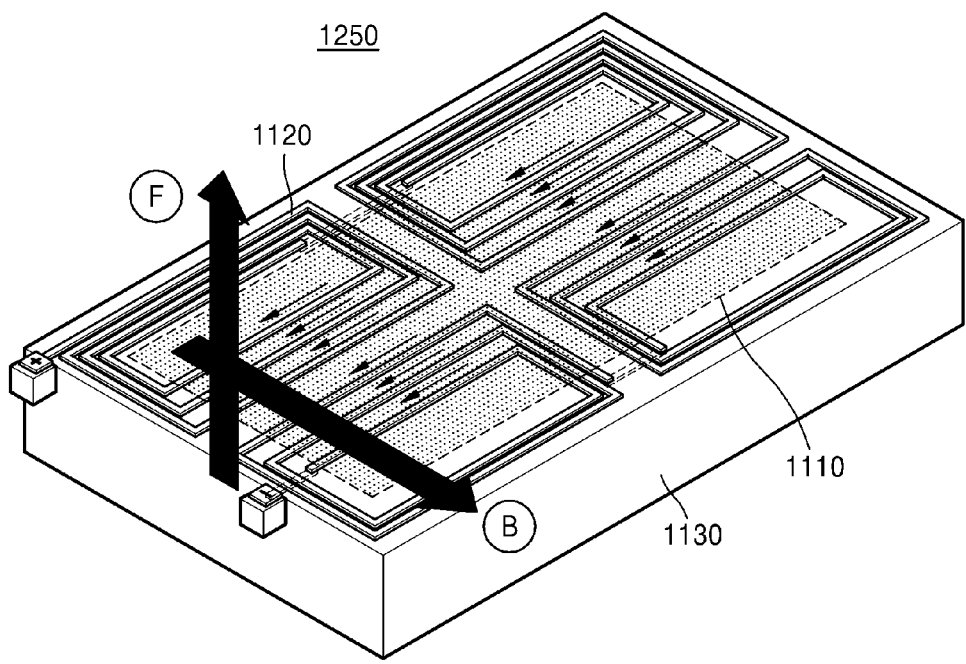
FIG. 14 is a perspective view showing a structure of an electro-acoustic transducer according to an exemplary embodiment.

FIG. 14 is a perspective view showing a structure of an electro-acoustic transducer 1250 according to an exemplary embodiment. The electro-acoustic transducer 1250 of FIG. 14 includes a plurality of patterns.

That is, in the vibrating unit 1110 of the electro-acoustic transducer 1250 of FIG. 14, the first coils 1120 may be disposed so that the repeated pattern depicted in FIG. 13 is consecutively formed. In the four repeated patterns depicted in FIG. 14, the location of the center of each of the repeated patterns is biased on a side of the first coils 1120.

That is, the first coils 1120 may be disposed such that, a portion of the first coils 1120 through which a current does not flow in a direction indicated by arrows is disposed to be located on a region of the vibrating unit 1110 that is not fixed, and a portion of the first coils 1120 through which the current flows in a direction besides the direction indicated by the arrows is disposed to be located on a region of the vibrating unit 1110 that is fixed on the supporting unit 1130. According to an exemplary embodiment, the vibrating unit 1110 of the electro-acoustic transducer 1250 may generate an acoustic signal by vibrating in the same direction by being located on a portion of the first coils 1120 where a current flows in a constant direction.

Figure 15A:
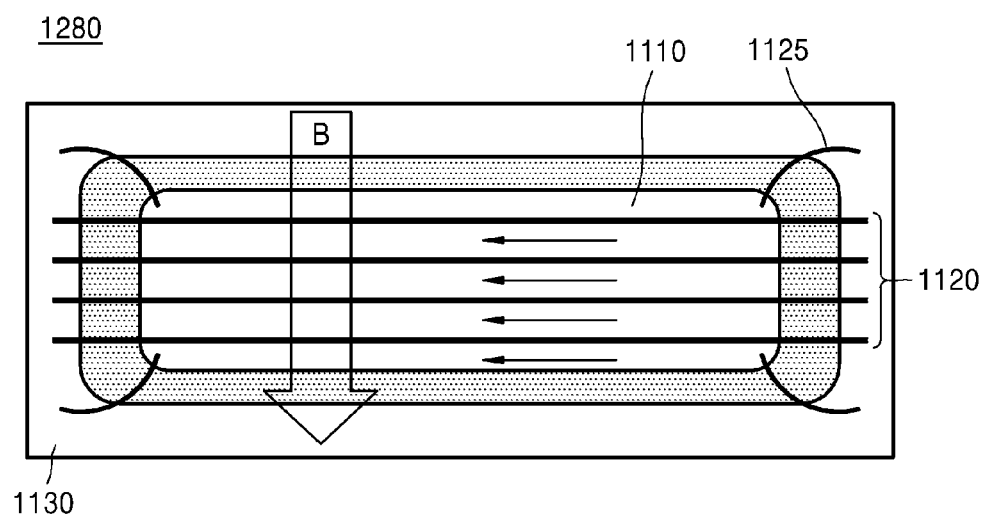
FIGS. 15A, 15B, 15C, and 15D show a structure of an electro-acoustic transducer according to an exemplary embodiment.
Figure 15B:
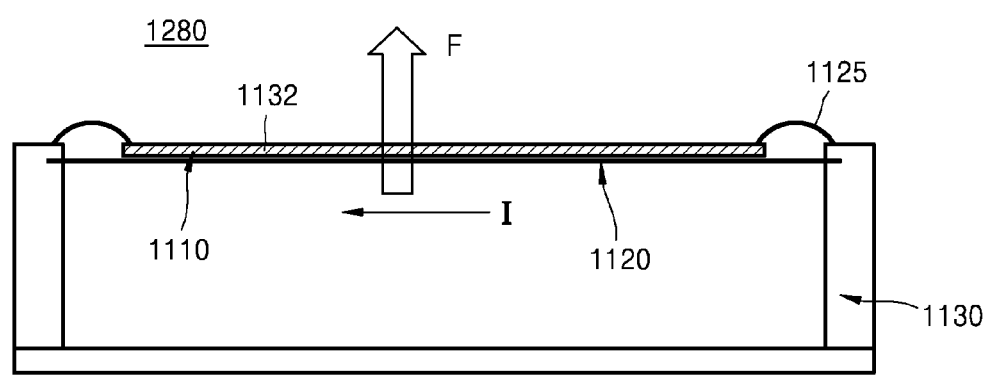

FIGS. 15A and 15B show the structure of an electro-acoustic transducer 1280 according to an exemplary embodiment. The electro-acoustic transducer 1280 depicted in FIG. 15 has a structure in which the vibrating unit 1110 includes a vibrating plate and a connection unit 1125 connects the vibrating unit 1110 to the supporting unit 1130.

FIG. 15A is a plan view of the electro-acoustic transducer 1280 according to an exemplary embodiment, and a shadow region indicates a region where the vibrating unit 1110 is separated from the supporting unit 1130. That is, the vibrating unit 1110 includes a vibrating plate formed of an elastic member, and is connected to the supporting unit 1130 by being combined with the flexible connection unit 1125. FIG. 15B is a lateral view of the electro-acoustic transducer 1280 according to an exemplary embodiment, and shows a configuration of connecting the vibrating unit 1110 to the supporting unit 1130 by the connection unit 1125. In FIG. 15B, the first coil 1120 is disposed on or proximate a lower surface 1132 of the vibrating unit 1110. However, the location of the first coil 1120 is not limited thereto.

In the electro-acoustic transducer 1280 depicted in FIG. 15, the electro-acoustic transducer 1280 is located in a magnetic field, and when a current flows through the first coil 1120, the Lorentz force is received in a direction indicated by "F". Accordingly, the vibrating unit 1110 vibrates while being connected to the connection unit 1125, and thus, may generate an acoustic signal.

Figure 15C:
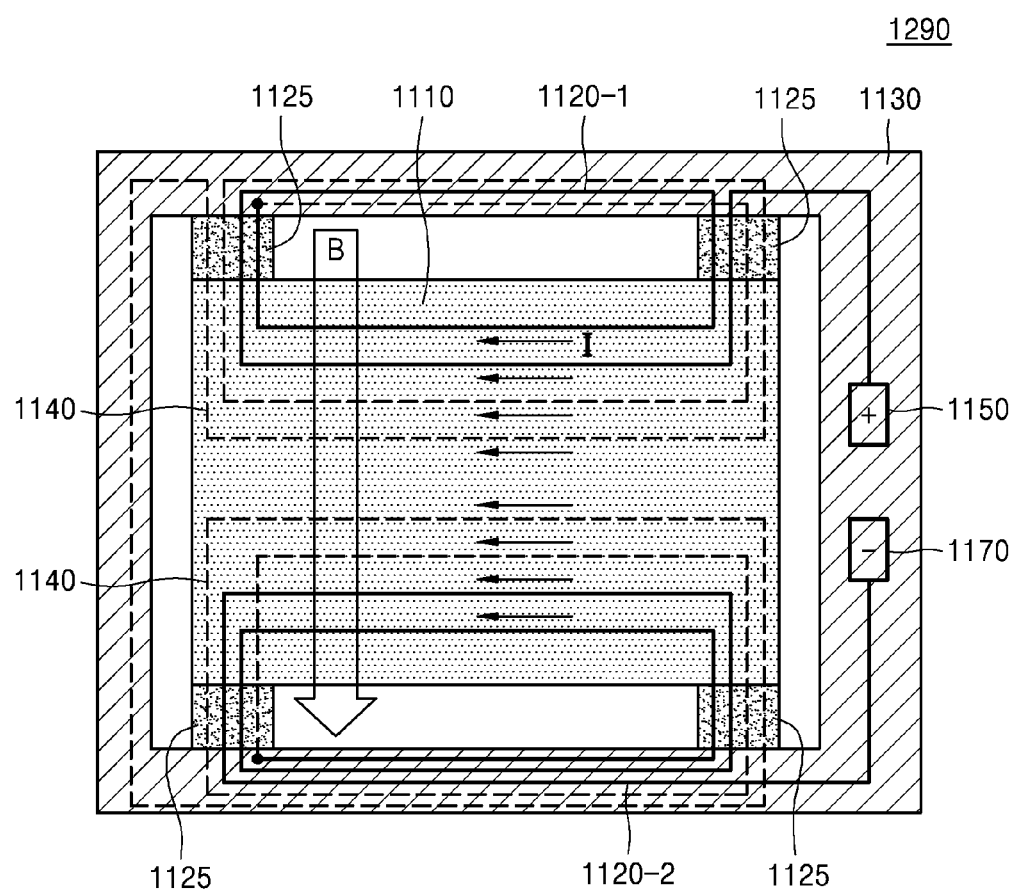

Meanwhile, FIG. 15C is a plan view of an electro-acoustic transducer 1290 related to an embodiment of the present disclosure. The electro-acoustic transducer 1290 may include a plurality of first coils 1120-1 and 1120-2 through which a current for generating an attraction force or a repulsion force with respect to a magnetic field of the MRI apparatus 110 flows. Also, the electro-acoustic transducer 1290 may include a vibrating plate 1110 on which at least a portion each of the first coils 1120-1 and 1120-2 is positioned and that vibrates in response to the an attraction force or the repulsion force that is generated by the first coils 1120-1 and 1120-2. Also, the electro-acoustic transducer 1290 may further include a supporting unit 1130 that fixes the vibrating plate 1110 and a connection unit 1125 that connects the vibrating plate 1110 and the supporting unit 1130. Remaining portions of each of the first coils 1120-1 and 1120-2 may be located at least one of upper surfaces of the supporting unit 1130 and the connection unit 1125.

In FIG. 15C, in the electro-acoustic transducer 1290 according to the embodiment of the present disclosure, the connection unit 1125 connects a portion of edges of the vibrating plate 1110 and the supporting unit 1130. However, the present disclosure is not limited to the case of FIG. 15C, that is, the connection unit 1125 according to the embodiment of the present disclosure may connect the entire edges of the vibrating plate 1110 and the supporting unit 1130. The vibrating plate 1110 may be formed of a elastic member, and thus, may be combine to the supporting unit 1130 by being combined with the flexible connection unit 1125.

The electro-acoustic transducer 1290 is operated generally similarly to the operation described with reference with FIG. 11. For example, at least a portion of each of the first coils 1120-1 and 1120-2 through which a current flows in a direction indicated by the arrows I may receive a Lorentz force F in a direction perpendicular to the vibrating plate 1110 in a magnetic field that is depicted in the direction "B" in FIG. 15C. Accordingly, the vibrating plate 1110 on which at least a portion of each of the first coils 1120-1 and 1120-2 may vibrate along the Lorentz force, and thus, may generate an acoustic signal.

For example, as depicted in FIG. 15C, at least a portion of each of the first coils 1120-1 and 1120-2 may be located on the upper surface of the vibrating plate 1110, and remaining portions of the first coils 1120-1 and 1120-2 may be located on upper surfaces of the connection unit 1125 and the supporting unit 1130.

Each of the first coils 1120-1 and 1120-2 may be disposed by forming repeated patterns. For example, as depicted in FIG. 15C, each of the first coils 1120-1 and 1120-2 may be disposed on the vibrating plate 1110, the connection unit 1125, and the supporting unit 1130 by forming a repeated pattern having a rectangular shape.

Also, the electro-acoustic transducer 1290 according to an exemplary embodiment may include second coils 1140 that are combined with the first coils 1120-1 and 1120-2 and through which a current outputted from one of the first coils 1120-1 and 1120-2 and a current inputted to one of the first coils 1120-1 and 1120-2 flow. For example, in FIG. 15C, portions indicated by solid lines may be the first coils 1120-1 and 1120-2 and portions indicated by dotted lines may be the second coils 1140.

As depicted in FIG. 15C, at least a portion of the second coils 1140 through which a current that is outputted from at least one of the first coils 1120-1 and 1120-2 or inputted to at least one of the first coils 1120-1 and 1120-2 may be located on a lower surface of the vibrating plate 1110. Also, remaining portions of the second coils 1140 may be located at least one of a lower surface of the supporting unit 1130 and the connection unit 1125. However, the second coils 1140 according to the current embodiment are not limited to the location indicated in FIG. 15C, that is, the second coils 1140 may be located on at least one of a lower surface of the vibrating plate 1110, the supporting unit 1130, and the connection unit 1125.

When a current inflows through an input terminal 1150 depicted in FIG. 15C, the current may flow through the first coil 1120-1 and may flow through the second coil 1140 that is connected to an end of the first coil 1120-1 on the supporting unit 1130. Next, the current that flows through the second coil 1140 may flow through the first coil 1120-2 through an end of the first coil 1120-2 on the supporting unit 1130. The current that inflows through the end of the first coil 1120-2 may flow through the first coil 1120-2 and may be outputted to an output terminal 1170. At this point, when an alternating current is inputted to the coil of the electro-acoustic transducer 1290, the direction of the current that flows through the coil of the electro-acoustic transducer 1290 may be periodically changed. Accordingly, when a current is inputted to the input terminal 1150 and is outputted to the output terminal 1170, the current may flows through the coil in a direction as depicted in FIG. 15C. However, when the direction of the current is changed, a current may be inputted to the output terminal 1170 and may be outputted to the input terminal 1150. At least a portion of the second coils 1140 through which a current flows in the direction as indicated by the arrows I may receive a Lorentz force in a direction perpendicular to the vibrating plate 1110 in the magnetic field that is generated in a direction indicated by the arrow B in FIG. 15C. Accordingly, the vibrating plate 1110 on which at least a portion of each of the first coils 1120-1 and 1120-2 and a portion of the second coils 1140 are disposed on both surfaces thereof may vibrates in response to the Lorentz force and may generate an acoustic signal.

The electro-acoustic transducer 1290 according to the current embodiment may include a printed circuit board (PCB) type. For example, at least a portion of the electro-acoustic transducer 1290 may include a flexible PCB (FPCB) type, and the first coils 1120-1 and 1120-2 and the second coils 1140 respectively may be included on an upper surface and a lower surface of the electro-acoustic transducer 1290. For example, the vibrating plate 1110 of the electro-acoustic transducer 1290 may include printed circuits (or printed wires) that are configured to flow currents in the same direction in order to receive the Lorentz force in the same direction in the magnetic field generated by a magnet of the MRI apparatus 110.

Meanwhile, in order to increase the Lorentz force by a magnetic field of the MRI apparatus 110, the number of wires disposed on the vibrating plate 1110 may be increased. However, the number of wires that may be disposed on the vibrating plate 1110 is limited. Thus, as depicted in FIG. 15C, the wires may be disposed on both sides of the vibrating plate 1110. Alternatively, the vibrating plate 1110 may include a plurality of boards on which wires are printed. The electro-acoustic transducer 1290 according to the exemplary embodiment may generate an acoustic signal in response to the Lorentz force by using a plurality of layered PCBs.

Figure 15D:
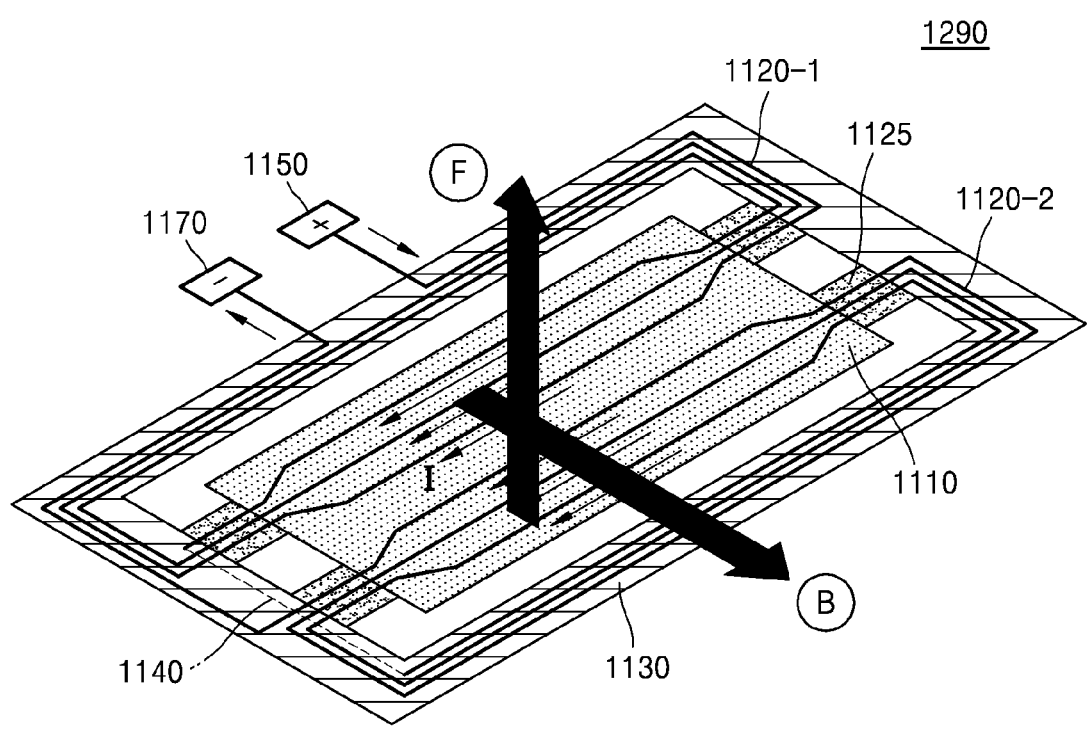

FIG. 15D is a perspective view of the electro-acoustic transducer 1290 according to the present invention. The electro-acoustic transducer 1290 of FIG. 15D includes two first coils 1120-1 and 1120-2 to correspond to the electro-acoustic transducer 1290 of FIG. 15C. Overlapped descriptions of elements that are described with reference to the electro-acoustic transducer 1290 of FIG. 15C will be omitted.

Meanwhile, as depicted in FIG. 15D, the first coils 1120-1 and 1120-2 of the electro-acoustic transducer 1290 may be disposed on upper surfaces of the vibrating plate 1110, the connection unit 1125, and the supporting unit 1130. Also, as depicted in FIG. 15D, the second coil 1140 of the electro-acoustic transducer 1290 may be disposed on a lower surface of the supporting unit 1130. In FIG. 15D, the second coil 1140 is indicated by dotted lines.

When a current is inputted to the input terminal 1150 depicted in FIG. 15D, the current may flow through the first coil 1120-1, and then, may flow through the second coil 1140 that is connected to an end of the first coil 1120-1 on the supporting unit 1130. Next, the current that flows through the second coils 1140 may flow through the first coil 1120-2 through an end of the first coil 1120-2. The current that is inputted through the end of the first coil 1120-2 may flow through the first coil 1120-2, and then, may be outputted to the output terminal 1170.

The vibrating plate 1110 of the electro-acoustic transducer 1290 may be realized in various types. That is, the vibrating plate 1110 may include a film or an elastic member. Besides above, the vibrating plate 1110 may be realized through various configurations to be able to vibrate in response to a Lorentz force.

In FIG. 15D, when a current flows in a direction indicated by "I" with respect to a magnetic field indicated by "B" of the MRI apparatus 110, the vibrating plate of the electro-acoustic transducer 1290 receives a Lorentz force in a direction indicated by "F". The vibrating plate 1110 of the electro-acoustic transducer 1290 vibrates in response to the Lorentz force, and thus, an acoustic signal may be generated by the vibration of the vibrating plate 1110.

As depicted in FIG. 15D, the electro-acoustic transducer 1290 may be disposed in an image-taking space or outside of the bore 111 so that the direction I of the current that flows through coils of the electro-acoustic transducer 1290 is not parallel (for example, to be perpendicular) to the magnetic field B that is generated by a magnet.

As depicted in FIGS. 15C and 15D, in the electro-acoustic transducer 1290 that includes two coils having a loop shape pattern, the electro-acoustic transducer 1290 may easily maintain a balance between the Lorentz forces that are applied to the vibrating plate 1110 by the current that flows through at least a portion of the coils and the magnetic field of the MRI apparatus 110.

Figure 16A:
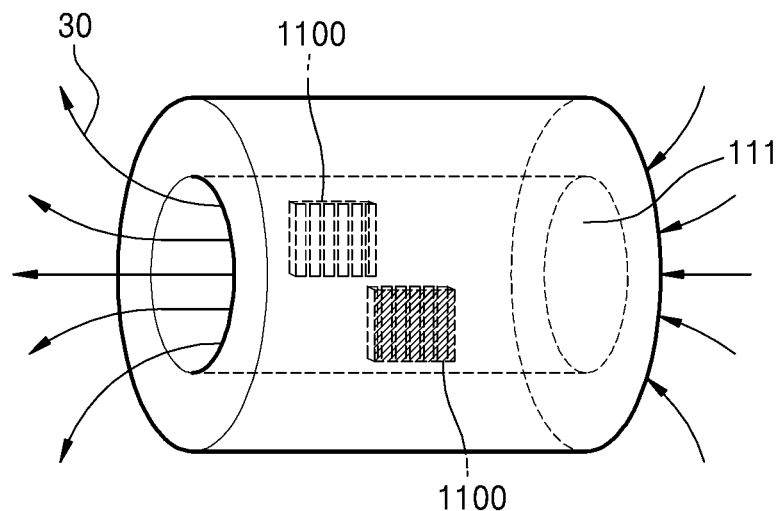
FIGS. 16A and 16B show positioning of an electro-acoustic transducer according to an exemplary embodiment.
Figure 16B:
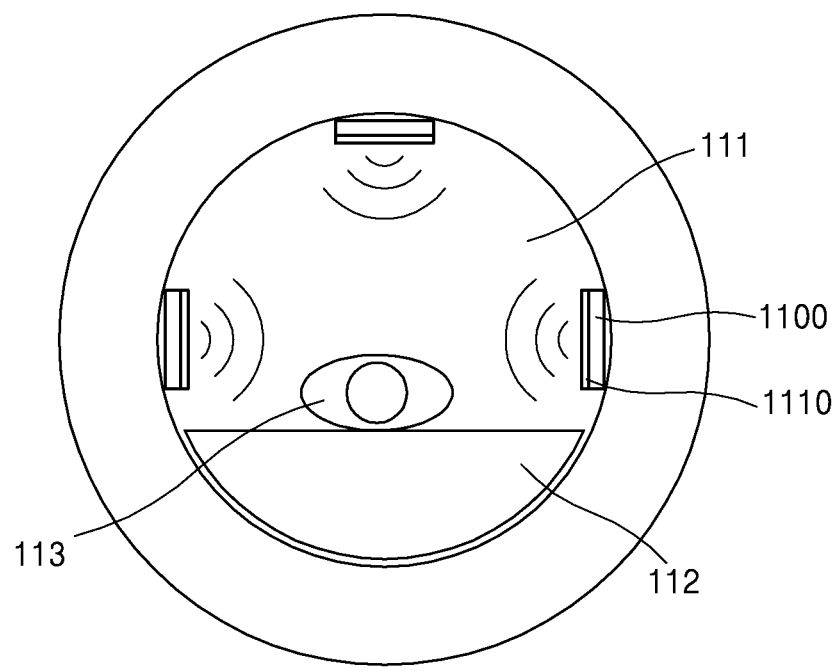

FIGS. 16A and 16B show positioning of the case type electro-acoustic transducer 1100 according to an exemplary embodiment in the bore 111 of the MRI apparatus 110. FIG. 16A is a lateral view of the bore 111, and FIG. 16B is a front or rear view of the bore 111.

In FIG. 16A, the electro-acoustic transducer 1100 may be positioned so that the direction 30 of the magnetic field generated by the magnet of the MRI apparatus 110 and the direction of the current flow are not parallel to each other. That is, as depicted in FIG. 16A, the electro-acoustic transducer 1100 may be positioned on a side of the bore 111 so that the direction of the magnetic field and the direction of the current are not parallel to each other. That is, an angle that is formed by the two directions may be greater than 0° and less than 90°.

In two electro-acoustic transducers 1100 depicted in FIG. 16A, a grey region indicates the electro-acoustic transducer 1100 that is positioned so that the vibrating unit 1110 faces an inner side of the bore 111.

In FIG. 16B, the electro-acoustic transducer 1100 generates an acoustic signal by being positioned in an upper area and both side areas of the bore 111. That is, to transmit the acoustic signal to the patient 113 positioned on the cradle 112, the electro-acoustic transducer 1100 may be positioned so that the vibrating unit 1110 vibrates in a direction towards the patient 113. As shown in FIG. 16A, the electro-acoustic transducer 1100 may generate an acoustic signal when the direction of the magnetic field and the direction of the current are not parallel to each other. The generation of the acoustic signal may be very effective when the electro-acoustic transducer 1100 is positioned so that two directions are perpendicular to each other.

Figure 17:
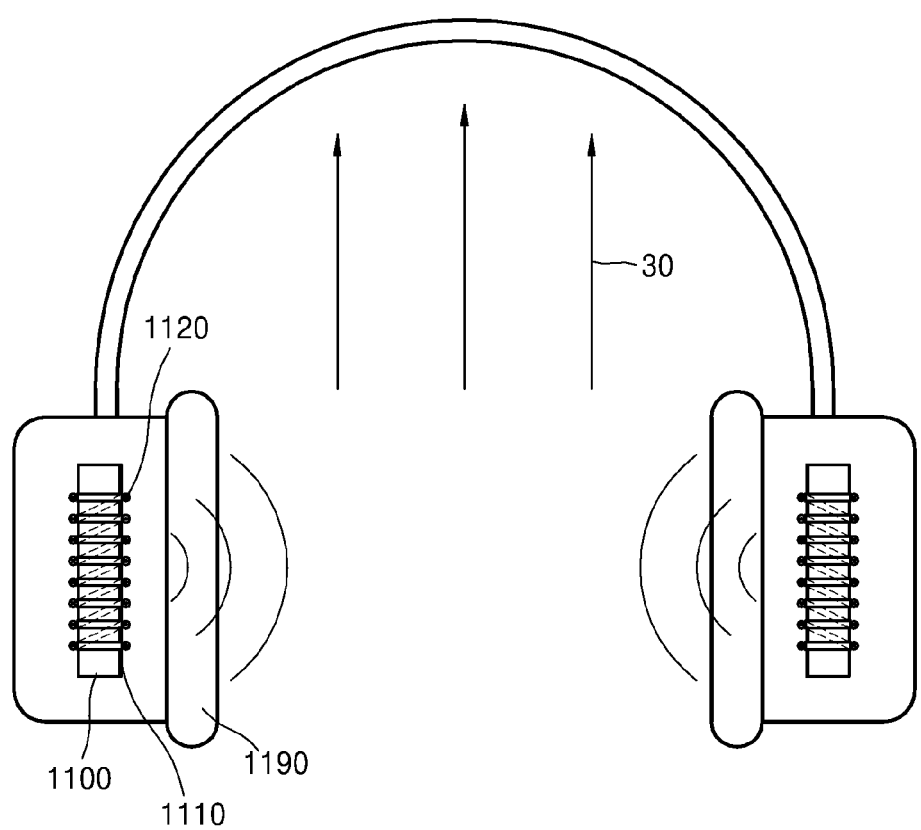
FIG. 17 is a drawing showing mounting of an electro-acoustic transducer in an acoustic output device according to an exemplary embodiment.

FIG. 17 is a drawing showing mounting of the electro-acoustic transducer 1100 in an acoustic output device 1190 according to an exemplary embodiment. In FIG. 17, the electro-acoustic transducer 1100 may be mounted on the acoustic output device 1190 so that the direction of a current that flows in the first coil 1120 located on the vibrating unit 1110 is not parallel to the direction 30 of a magnetic field.

According to an exemplary embodiment, the electro-acoustic transducer 1100 may be mounted on the acoustic output device 1190 such as a headset, and an acoustic signal generated from the electro-acoustic transducer 1100 may be directly transmitted to the patient 113.

Figure 18A:
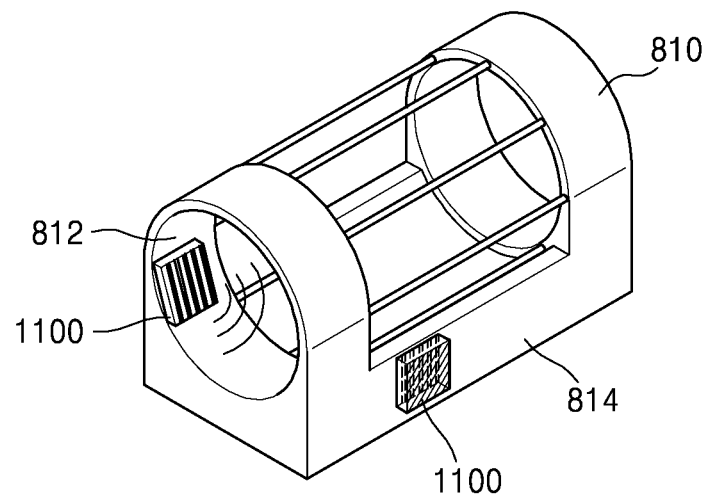
FIGS. 18A and 18B show positioning of an electro-acoustic transducer according to an exemplary embodiment.

FIG. 18A is a perspective view showing positioning of the electro-acoustic transducer 1100 on a head RF coil 810 according to an exemplary embodiment. The electro-acoustic transducer 1100 according to an exemplary embodiment, as depicted in FIG. 18A, may be positioned on an inner side surface 812 or an outer side surface 814 of the head RF coil 810. When the electro-acoustic transducer 1100 is positioned on the inner side surface of the head RF coil 810, the electro-acoustic transducer 1100 may generate an acoustic signal in a direction towards the patient 113.

A dark region is a rear surface of the electro-acoustic transducer 1100. According to an exemplary embodiment, the electro-acoustic transducer 1100 positioned in the head RF coil 810 may be positioned to face the patient 113 as depicted in FIG. 16A, and also, may output an acoustic signal outwards of the head RF coil 810 by being positioned in a direction opposite to the patient 113.

Figure 18B:
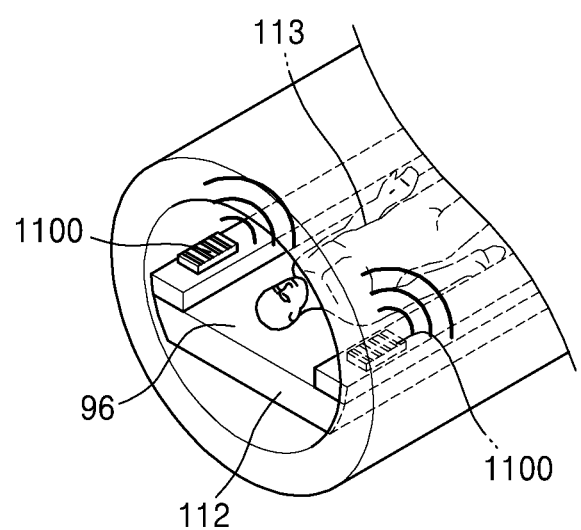

FIG. 18B is a perspective view showing positioning of the electro-acoustic transducer 1100 on the cradle 112. The electro-acoustic transducer 1100 according to an exemplary embodiment may transmit an acoustic signal to the patient 113 by being positioned at a head portion 96 of the cradle 112. The electro-acoustic transducer 1100 mounted on the head portion 96 may be positioned so that the direction of a current flow is not parallel to the direction of a magnetic field.

Figure 19A:
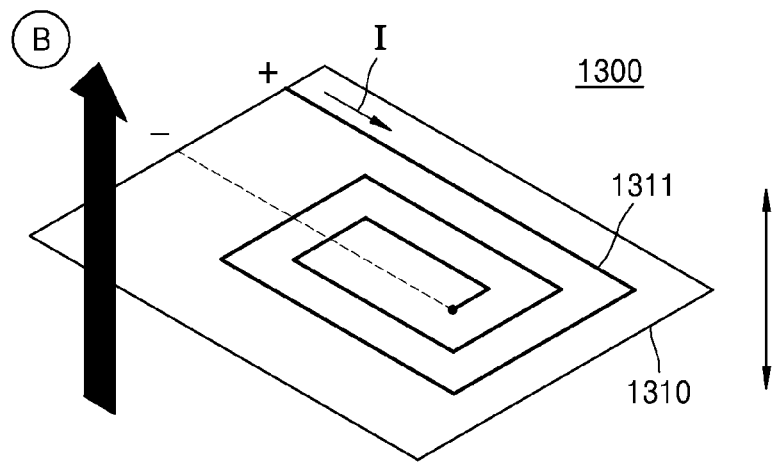
FIGS. 19A, 19B, and 19C show patterns of an electro-acoustic transducer according to an exemplary embodiment.
Figure 19B:
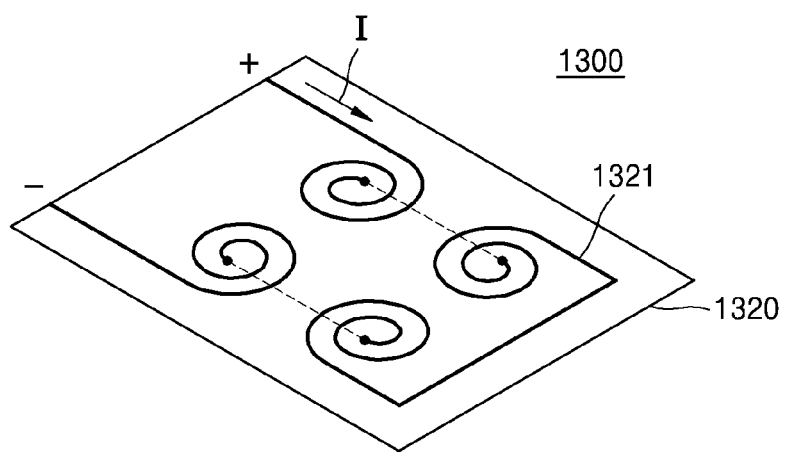
Figure 19C:
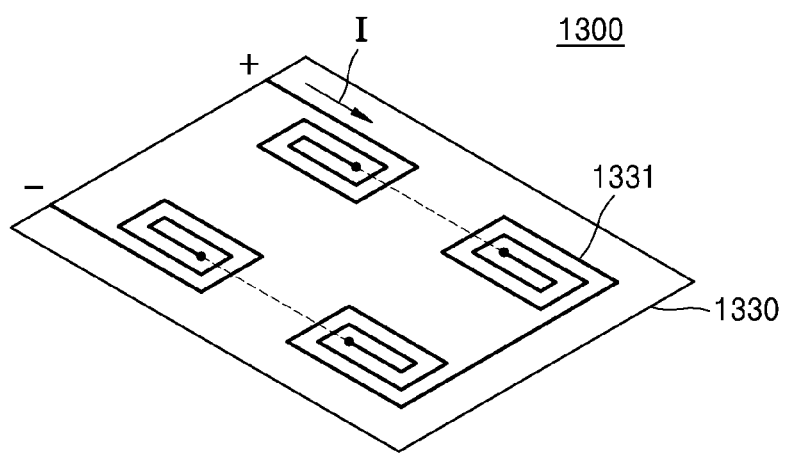

FIGS. 19A, 19B, and 19C show a pattern of an electro-acoustic transducer 1300 according to an exemplary embodiment. The electro-acoustic transducer 1300 according to an exemplary embodiment may include a vibrating unit 1310, 1320, and 1330, respectively, and a coil that is disposed on the vibrating unit 1310, 1320, and 1330 and through which a current flows. FIGS. 19A, 19B, and 19C respectively show various patterns 1311, 1321, and 1331 formed on the vibrating units 1310, 1320, and 1330 of the electro-acoustic transducer 1300. The vibrating units 1310, 1320, and 1330 may be formed of a non-magnetic material or a feeble magnetic material, and as described above, may include a vibrating film or a vibrating plate.

In FIGS. 19A, 19B, and 19C, solid lines indicate coils through which a current flows on the vibrating units 1310, 1320, and 1330, and dotted lines indicate coils through which a current flows on lower surfaces of the vibrating units 1310, 1320, and 1330.

The electro-acoustic transducer 1300 according to an exemplary embodiment may include a first coil that includes at least one repeating pattern and through which a current that generates an attractive force or a repulsive force with respect to a magnetic field of the MRI apparatus 110 flows and a second coil through which the same current that is input to the first coil flows. That is, in FIGS. 19A, 19B, and 19C, the parts shown by solid lines may be first coils, and the parts shown by dotted lines may be second coils. However, as described above, since the second coil is a coil through which the same current input to the first coil and the current output from the first coil flows, the first and second coils are not limited to the coils indicated by the solid lines and the dotted lines as depicted above.

For example, the second coil, through which the current input to the first coil and the current output from the first coil flow, may include not only the parts shown by dotted lines on lower surfaces of the vibrating units 1310, 1320, and 1330 in FIGS. 19A, 19B, and 19C, but also the parts shown by solid lines from an input terminal indicated by "+" to a point where the first pattern of at least one of the repeating patterns begins. For example, in FIG. 19B, the second coil may include not only the parts shown by dotted lines, but also the parts besides the screw pattern parts of the coil. The second coil may include all coils besides at least one repeating pattern disposed on the lower surfaces of the vibrating units 1310, 1320, and 1330.

The electro-acoustic transducer 1300 depicted in FIGS. 19A, 19B, and 19C may be positioned in the magnetic field of the MRI apparatus 110 so that the magnetic field of the MRI apparatus 110 is perpendicular (in FIG. 19A, a vertical upward direction) to the vibrating units 1310, 1320, and 1330. When a current is input to the first coil of the electro-acoustic transducer 1300, the first coil generates a magnetic field having a constant direction (the Ampere's right-handed screw rule direction). That is, when a current flows in the first coil in a direction indicated by the arrow, the direction of the magnetic field that is generated by the first coil is a downward direction (in a direction opposite to the magnetic field of the MRI apparatus 110) perpendicular to the vibrating units 1310, 1320, and 1330.

As described above, when an AC current is input to the electro-acoustic transducer 1300, the direction of the current varies every moment, and accordingly, the vibrating units 1310, 1320, and 1330 generate magnetic fields having the same direction as or opposite direction to the magnetic field of the MRI apparatus 110. Accordingly, the vibrating units 1310, 1320, and 1330 may generate an acoustic signal by vibrating due to an attractive force or a repulsive force of the MRI apparatus 110.

The first coil disposed on the vibrating units 1310, 1320, and 1330 may form at least one pattern 1311, 1321, and 1331 by consecutively being disposed in a predetermined direction. That is, as depicted in FIGS. 19A, 19B, and 19C, the coil may be disposed on the vibrating units 1310, 1320, and 1330 by being wound in a predetermined clock direction. Thus, the coil may generate a uniform magnetic field in a predetermined direction (Ampere's right-handed screw rule direction) when a current flows therethrough.

In FIGS. 19A, 19B, and 19C, the first coils form rectangular shape patterns 1311 and 1331 on the vibrating units 1310 and 1330, and in FIG. 19B, the first coil forms a screw shape pattern on the vibrating unit 1320. As described above, at least one repeating pattern of the first coil may be formed on the vibrating units 1310, 1320, and 1330.

According to an exemplary embodiment, the electro-acoustic transducer 1300 may further include a supporting unit (not shown), the supporting unit being combined with both edges or corners of the vibrating units 1310, 1320, and 1330 so that the vibrating units 1310, 1320, and 1330 vibrate according to a interacting force with the MRI apparatus 110. The supporting unit according to an exemplary embodiment may be realized similarly to the supporting unit 1130 described with reference to FIG. 11.

According to the MRI acoustic system, the electro-acoustic transducer, and the acoustic output device of an exemplary embodiment, an acoustic signal may be effectively transmitted to a patient located in a bore of the MRI apparatus by using a magnetic field of the MRI apparatus instead of using a magnetic material to generate the acoustic signal.

Therefore, an acoustic signal in a wide frequency band may be output without affecting the magnetic field of the MRI apparatus. Although the intensity of the magnetic field is changed by moving the cradle, an acoustic signal having a constant magnitude may be generated.

Also, the costs for manufacturing the MRI acoustic system may be reduced when compared to a piezo-electric speaker, a related art loud speaker, or a related art dynamic speaker by not using a magnetic material such as a magnet or an iron body. Also, the durability of the electro-acoustic transducer, the acoustic output device, and the MRI acoustic system may be increased by blocking a current input to the electro-acoustic transducer according to the intensity of a magnetic field of the MRI apparatus or the position of the cradle.

Although a few exemplary embodiments have been shown and described, it would be appreciated by those skilled in the art that various changes in form and detail may be made in these exemplary embodiments without departing from the spirit and scope of the disclosure, the scope of which is defined by the claims and their equivalents.

What is claimed is:

1. A magnetic resonance imaging (MRI) acoustic system comprising:
 a magnet that is included in a bore having an image-taking space where an object is able to be accommodated and that forms a magnetic field in the image-taking space to obtain an MR image of the object;
 an electro-acoustic transducer that is located outside of the bore, and comprises coils through which a current for generating an attraction force or a repulsion force with respect to the magnetic field generated by the magnet flows, and a vibrating plate that vibrates in response to the attraction force or the repulsion force; and
 a controller that controls an intensity of the current inputted to the electro-acoustic transducer to generate a sound by using the magnetic field that is generated by the magnet.

2. The MRI acoustic system of claim 1, wherein the electro-acoustic transducer is located outside of the bore so that the direction of a current that flows through the coils is not parallel to the magnetic field generated by the magnet.

3. The MRI acoustic system of claim 1, wherein the bore has a column shape,
 the image-taking space in the bore is configured to accommodate the object through an opening in at least one of a top surface and a bottom surface of the bore,
 the electro-acoustic transducer is located on the at least one of the top surface and the bottom surface of the bore.

4. The MRI acoustic system of claim 3, wherein the electro-acoustic transducer is located on the at least one of the top surface and the bottom surface of the bore so that the direction of a current that flows through the coils is perpendicular to the magnetic field generated by the magnet.

5. The MRI acoustic system of claim 1, wherein the electro-acoustic transducer is configured so that the vibrating plate vibrates in a direction parallel to the direction of moving a cradle for accommodating the object in the image-taking space.

6. An electro-acoustic transducer that uses a magnetic field of a magnetic resonance imaging (MRI) apparatus, the electro-acoustic transducer comprising:
 a plurality of first coils through which a current for generating an attraction force or a repulsion force with respect to a magnetic field of the MRI apparatus flows;
 a vibrating plate on which at least a portion of each of the first coils is located and that vibrates in response to the attraction force or the repulsion force generated by the first coils;
 a supporting unit that fixes the vibrating plate;
 a connection unit that connects the vibrating plate and the supporting unit; and
 a second coil that is combined with the first coils, and through which a current outputted from at least one of the first coils and a current inputted to one of the remaining first coils flow.

7. The electro-acoustic transducer of claim 6, wherein at least a portion of each of the first coils is located on the upper surface of the vibrating plate,
 the remaining portion of each of the first coils is located on upper surfaces of the supporting unit and the connection unit,
 at least a portion of the second coil is located on a lower surface of the vibrating plate; and
 the remaining portion of the second coil is located on lower surfaces of the supporting unit and the connection unit.

8. The electro-acoustic transducer of claim 6, wherein each of the first coils is disposed in repeated patterns.

9. A magnetic resonance imaging (MRI) acoustic system comprising:
 a magnet which is disposed in a bore having an image acquisition space for accommodating an object, and forms a magnetic field in the image acquisition space to obtain an MR image of the object; and
 an electro-acoustic transducer comprising:

first coils through which a current for generating an attraction force or a repulsion force with respect to the magnetic field of the MRI apparatus flows, a vibrating plate on which a portion of each of the first coils is located, and which vibrates in response to the attraction force or the repulsion force generated by the first coils, a supporting unit that fixes the vibrating plate, a connection unit that connects the vibrating plate and the supporting unit, and a second coil that is connected to the first coils, and through which a current output from one of the first coils and a current input to another one of the first coils flows.

10. The MRI acoustic system of claim 9, wherein the portion of each of the first coils is located on an upper surface of the vibrating plate, a remainder of each of the first coils is located on upper surfaces of the supporting unit and the connection unit, a portion of the second coil is located on a lower surface of the vibrating plate; and a remainder of the second coil is located on lower surfaces of the supporting unit and the connection unit.

11. The electro-acoustic transducer of claim 10, wherein each of the first coils is disposed in repeated patterns, on the upper surfaces of the vibrating plate, the supporting unit, and the connection unit.

* * * * *